US005635601A

United States Patent [19]

Moyle et al.

[11] Patent Number: 5,635,601

[45] Date of Patent: Jun. 3, 1997

[54] BETA-8 INTEGRIN SUBUNIT ANTIBODIES

[75] Inventors: Matthew Moyle, Walnut Creek; John W. McLean, San Francisco, both of Calif.

[73] Assignee: Genentech, Inc., South San Francisco, Calif.

[21] Appl. No.: 454,455

[22] Filed: May 30, 1995

Related U.S. Application Data

[62] Division of Ser. No. 193,989, Feb. 9, 1994, which is a continuation of Ser. No. 4,142, Jan. 13, 1993, abandoned, which is a continuation of Ser. No. 670,607, Mar. 14, 1991, abandoned.

[51] Int. Cl.[6] ........................ A61K 39/395; C07K 16/28; C12P 21/08; C12N 15/06

[52] U.S. Cl. .................................... 530/388.2; 530/388.7; 530/389.6; 435/70.21; 435/172.2; 424/139.1; 424/144.1; 424/158.1; 424/172.1

[58] Field of Search ............................ 424/139.1, 143.1, 424/144.1, 158.1, 172.1; 435/69.6, 70.21, 172.2, 240.27; 530/387.9, 388.2, 388.22, 388.7, 389.2, 389.6

[56] References Cited

U.S. PATENT DOCUMENTS

| | | | |
|---|---|---|---|
| 4,394,443 | 7/1983 | Weissman et al. | 435/6 |
| 4,474,893 | 10/1984 | Reading | 436/547 |

OTHER PUBLICATIONS

Sevier et al. Clin Chem 27111:1797–1806 1981.

Seaver Genetic Engineering, vol. 14 (14): 10&21 1994.

Albelda et al., "Integrins and other cell adhesion molecules" *FASEB–J* 4 (11):2868–2880 (1990).

Bates et al., "Individual Embryonic Fibroblasts Express Multiple β Chains in Association with the αv Integrin Subunit" *Journal of Biological Chemistry* 266 (28):18593–18599 (1991).

Bodary et al., "The integrin β 1 subunit associates with the vitronectin receptor α v subunit to form a novel vitronectin receptor in a human embryonic kidney cell line" *Journal of Biological Chemistry* 265 (11):5938–5941 (1990).

Bossy et al., "Chick integrin α V subunit molecular analysis reveals high conservation of structural domains and association with nultiple β subunits in embryo fibroblasts" *Biochemistry* 29 (44):10191–10198 (1990).

Cheresh et al., "A Novel Vitronectin Receptor Integrin (αvβx) Is Responsible for Distinct Adhesive Properties of Carcinoma Cells" *Cell* 57:59–69 (1989).

Chuong, "Differential roles of multiple adhesion molecules in cell migration: granule cell migration in cerebellum" *Experientia* 46 (9):892–899 (1990).

Fitzgerald and Phillips, "The Molecular Biology of Platelet and Endothelial Cell Adhesion Receptors" *Molecular Biology, Immunology, Biochemistry, & Pathology,* New York:Alan R. Liss, Inc. pp. 387–418 (1988).

Fitzgerald et al., "Protein Sequence of Endothelial Glycoprotein IIIa Derived from a cDNA Clone" *Journal of Biological Chemistry* 262:3936–3939 (1987).

Freed et al., "A novel integrin β subunit is associated with the vitronectin receptor α subunit (αv) in human osteosarcoma cell line and is a substrate for protein kinase C" *EMBO Journal* 8 (10):2955–2965 (1989).

Hatten, "Riding the glial monorail: a common mechanism for glial–guided neuronal migration in different regions of the developing mammalian brain" *Trends in Neurosciences* 13 (5):179–184 (1990).

Hemler, "VLA proteins in the integrin family: structures, functions, and their role on leukocytes" *Annu. Rev. Immunol.* 8:365–400 (1990).

Hogervorst et al., "Cloning and sequence analysis of β–4 cDNA: an integrin subunit that contains a unique 118 kd cytoplasmic domain" *EMBO Journal* 9 (3):765–770 (1990).

Horton, "Current Status Review Vitronectin receptor: tissue specific expression or adaptation to culture?" *Int. J. Exp. Pathol.* 71:741–759 (1990).

Hynes, "Integrins: A Family of Cell Surface Receptors" *Cell* 48:549–554 (1987).

Hynes, "Integrins: versatility, modulation, and signaling in cell adhesion" *Cell* 69 (1):11–25 (1992).

Jessell, "Adhesion Molecules and the Hierarchy of Neural Development" *Neuron* 1:3–13 (1988).

Kajiji et al., "A Novel Integrin (αEβ4) from human epithelial cells suggests a fourth family of integrin adhesion receptors" *EMBO Journal* 8 (3):673–680 (1989).

Kieffer et al., "Platelet Membrane Glycoproteins: Functions in Cellular Interactions" *Annu. Rev. Cell Biol.* 6:329–357 (1990).

Kishimoto et al., "Cloning of the β Subunit of the Leukocyte Adhesion Proteins: Homology to an Extracellular Matrix Receptor Defines a Novel Supergene Family" *Cell* 48:681–690 (1987).

McLean et al., "cDNA sequence of the human integrin β 5 subunit" *Journal of Biological Chemistry* 265(28):1712–1713 (1990).

Moyle et al., "Cloning and expression of a divergent integrin subunit β8" *Journal of Biological Chemistry* 266 (29):11650–11658 (1991).

Phillips et al., "The Platelet Membrane Glycoprotein IIb–IIIa Complex" *Blood* 71 (4):831–843 (1988).

Plantefaber and Hynes, "Changes in integrin receptors on oncogenically transformed cells" *Cell* 56:281–290 (1989).

Ramaswamy et al., "Cloning, primary structure and properties of a novel human integrin β subunit" *EMBO Journal* 9 (5):1561–1568 (1990).

(List continued on next page.)

*Primary Examiner*—Robert D. Budens
*Assistant Examiner*—Julie E. Reeves
*Attorney, Agent, or Firm*—Walter H. Dreger

[57] ABSTRACT

The cDNA encoding a novel beta integrin subunit, called the beta-8 integrin subunit, has been isolated from rabbit and human tissue and sequenced. Provided herein is nucleic acid sequence of the beta-8 integrin subunit useful as a diagnostic and in the recombinant preparation of beta-8 integrin subunit and alpha-beta integrin complexes. The beta-8 integrin subunit is used in the preparation and purification of antibodies thereto, and in diagnostic assays.

6 Claims, 13 Drawing Sheets

OTHER PUBLICATIONS

Rathgen, "A neurite outgrowth–promoting molecule in developing fiber tracts" *Trends in Neurosciences* 11 (5):183–184 (1988).

Ruoslahti, "Integrins" *J. Clin. Invest.* 87:1–5 (1991).

Saga et al., "Enhanced Fibronectin Receptor Expression in Rous Sarcoma Virus–induced Tumors" *Cancer Research* 48:5510–5513 (1988).

Sanes, "Extracellular Matrix Molecules that Influence Neural Development" *Ann. Rev. Neurosci.* 12:491–516 (1989).

Sheppard et al., "Complete amino acid sequence of a novel integrin β subunit (β6) identified in epithelial cells using the polymerase chain reaction" *Journal of Biological Chemistry* 265 (20):1150–1150 (1990).

Smith et al., "Purification and functional characterization of integrin αv β5: An adhesion receptor for vitronectin" *Journal of Biological Chemistry* 265 (19):1100–1101 (1990).

Suzuki et al., "Amino acid sequence of a novel integrin β 4 subunit and primary expression of the mRNA in epithelial cells" *EMBO Journal* 9 (3):757–763 (1990).

Tamkun et al., "Structure of Integrin, a Glycoprotein Involved in the Transmembrane Linkage between Fibronectin and Actin" *Cell* 46:271–282 (1986).

Yuan et al., "Cloning and sequence analysis of a novel β 2–related integrin transcript from T lymphocytes: homology of integrin cysteine–rich repeats to domain III of laminin B chains" *Int–Immunol* (published erratum appears in Int Immunol 1991 Dec.; 3(12):1373–4) 2(11):1097–1108 (1990).

```
GGCGATGGCT CGCGCGGAGC CTGCGGGCGT CGGCAGGCGC TGCTAGGGCG CTCCCGGAGC CGCCTCCCCG GGCTGCTGGC
GCCCAGAGCT TCCTCCCTGG CCCGCCGGGC GCGGGGCTGC AAGCCGGGGG ACGTGGCCTC TCCTGCCCAC CTGTGGAAGG
AGCTCGCGCC GATGGCTGCG CCCTCCGGCC TCGCAGGCGT CCCCTCCCAC TAAGGCAGCA TCACCCAGCG AATGTACTTT
AGGGTGGTTT CCCCCTCCCC AGCTTCGGGC TTTGTTTGGG TTTGATTGTG TTTGGCTCTC CGCTAAGCTG ATTTATGCAG
CACAAGCCCC ATCGGCTGGC GAGAAACAAA AGCTCTTTTC TTTGTCCCGG GAGCGGGCTT GCGGAGCCCC GGCTCGCGTC
GGCGACCGGG CCATCGGCCG TCGCGGGAGG CGCTGCTGGC CGAGGCCGCG CCGAGCTGGG AGGGCCGCGG GGGCCCTGGG
ATGCCGAGCG GCGCCGGGGC CCGCGTACCT GCACCGCCTG CCGGGGAGCG CCTGCCAGGC CTGCTGGAGA CGTCCTAGCG
GGCTCGGCCC GGGCCCCGAG GTCGCCCGGG AGGCCGAGCG CGCGTCCCCA GAGCGGCCAG GCGGCGGGCG CGGGGCGGGC

CGCTGTGCAG   650

T   ATG TGC GGC TCG GCC CTG GGT CTC CCT CCC GCC GCA TTC GTC CGC CTG CGC AGC TGC CGG CCA
    MET CYS GLY SER ALA LEU GLY LEU PRO PRO ALA ALA PHE VAL ARG LEU ARG SER CYS ARG PRO
     1               5                  10                  15                  20

GGT CCT GCG GCG TTC CTC CGG GCG GCC TGG GTG CTC TCA CTT GTT CTC GGA CTG GGT CGA AGC GAA
GLY PRO ALA ALA PHE LEU ARG ALA ALA TRP VAL LEU SER LEU VAL LEU GLY LEU GLY ARG SER GLU
            25                  30                  35                  40

AAC AGT AGA TGC GCA TCC TCC CAT GCT GTG TCG TGT TCC GAG TGC CTT GCG CTG GGT CCA GAC TGT
ASN SER ARG CYS ALA SER SER HIS ALA VAL SER CYS SER GLU CYS LEU ALA LEU GLY PRO ASP CYS
     45                  50                  55                  60                  65

GGA TGG TGT GTT CAC GAG GAT TTC ATC TCA GGT GGA CCA AGG AGT GAG CGC TGT GAT ATT GTT TCC
GLY TRP CYS VAL HIS GLU ASP PHE ILE SER GLY GLY PRO ARG SER GLU ARG CYS ASP ILE VAL SER
                70                  75                  80                  85
```

FIG. 1A

```
AAT TTA ATA AGC AAA GGC TGC CCG GTG GAT TCA ATA GAA TAC CCA TCT GTG CAT GTG ACA ATT CCA
ASN LEU ILE SER LYS GLY CYS PRO VAL ASP SER ILE GLU TYR PRO SER VAL HIS VAL THR ILE PRO
         90                  95                  100                 105

AGT GAA AAT GAA GTT AAT ACC CAG GTG ACA CCA GGA GAA GTG TCG ATT CAG CTG CGA CCA GGA GCT
SER GLU ASN GLU VAL ASN THR GLN VAL THR PRO GLY GLU VAL SER ILE GLN LEU ARG PRO GLY ALA
110                 115                 120                 125                 130

GCA GCT AAT TTT ATG CTG AAA ATT CAT CCG CTG AAG AAA TAT CCT GTG GAT CTT TAT TAT CTG GTA
ALA ALA ASN PHE MET LEU LYS ILE HIS PRO LEU LYS LYS TYR PRO VAL ASP LEU TYR TYR LEU VAL
            135                 140                 145                 150

GAT GTC TCA GCA TCA ATG CAC AAC AAT ATA GAA AAA TTA AAT TCT GTT GGA AAT GAC TTA TCT AGA
ASP VAL SER ALA SER MET HIS ASN ASN ILE GLU LYS LEU ASN SER VAL GLY ASN ASP LEU SER ARG
    155                 160                 165                 170                 175

AAA ATG GCA TTT TTC TCC CGT GAC TTC CGC CTT GGG TTC GGC TCC TAT GTT GAT AAA ACA GTC TCA
LYS MET ALA PHE PHE SER ARG ASP PHE ARG LEU GLY PHE GLY SER TYR VAL ASP LYS THR VAL SER
                180                 185                 190                 195

CCA TAC ATC AGT ATC CAC CCA GAA AGG ATT CAC AAC CAA TGC AGT GAC TAC AAC TTA GAC TGC ATG
PRO TYR ILE SER ILE HIS PRO GLU ARG ILE HIS ASN GLN CYS SER ASP TYR ASN LEU ASP CYS MET
        200                 205                 210                 215

CCC CCC CAC GGA TAC ATC CAT GTG CTG TCC CTG ACG GAG AAC ATC ACG GAG TTC GAG CGA GCT GTG
PRO PRO HIS GLY TYR ILE HIS VAL LEU SER LEU THR GLU ASN ILE THR GLU PHE GLU ARG ALA VAL
220                 225                 230                 235                 240

CAC AGA CAG AAA ATC TCT GGC AAC ATC GAC ACA CCC GAA GGA GGC TTT GAT GCC ATG CTG CAG GCT
HIS ARG GLN LYS ILE SER GLY ASN ILE ASP THR PRO GLU GLY GLY PHE ASP ALA MET LEU GLN ALA
            245                 250                 255                 260
```

FIG. 1B

```
GCC GTC TGC GAG AGT CAC ATC GGA TGG CGA AAA GAA GCT AAA AGA TTG CTG CTG GTG ATG ACG GAT
ALA VAL CYS GLU SER HIS ILE GLY TRP ARG LYS GLU ALA LYS ARG LEU LEU LEU VAL MET THR ASP
    265                 270                 275                 280                 285

CAG ACA TCT CAT CTG GCC CTT GAT AGC AAG TTG GCA GGC ATT GTG GTG CCG AAT GAT GGA AAT TGC
GLN THR SER HIS LEU ALA LEU ASP SER LYS LEU ALA GLY ILE VAL VAL PRO ASN ASP GLY ASN CYS
                290                 295                 300                 305

CAT CTG AGA AAC AAC GTC TAC GTC AAG TCC ACA ACC ATG GAA CAT CCC TCA CTA GGC CAA CTT TCA
HIS LEU ARG ASN ASN VAL TYR VAL LYS SER THR THR MET GLU HIS PRO SER LEU GLY GLN LEU SER
        310                 315                 320                 325

GAG AAA TTA ATA GAC AAC AAC ATC AAT GTC ATC TTT GCA GTT CAA GGA AAA CAG TTT CAT TGG TAT
GLU LYS LEU ILE ASP ASN ASN ILE ASN VAL ILE PHE ALA VAL GLN GLY LYS GLN PHE HIS TRP TYR
330                 335                 340                 345                 350

AAG GAC CTT CTA CCC CTC TTG CCG GGT ACC ATT GCT GGT GAA ATA GAA TCA AAG GCT GCA AAC CTC
LYS ASP LEU LEU PRO LEU LEU PRO GLY THR ILE ALA GLY GLU ILE GLU SER LYS ALA ALA ASN LEU
            355                 360                 365                 370

AAT AAT TTG GTA GTA GAA GCC TAT CAG AAA CTC ATT TCA GAA GTG AAA GTG CAG GTG GAA AGC AAA
ASN ASN LEU VAL VAL GLU ALA TYR GLN LYS LEU ILE SER GLU VAL LYS VAL GLN VAL GLU SER LYS
    375                 380                 385                 390                 395

GTG CCA GGC GTC TAC TTT AAC GTC ACA GCC ATC TGT CCA GAT GGA GCC AGG AAG CTG GGC ATG GAA
VAL PRO GLY VAL TYR PHE ASN VAL THR ALA ILE CYS PRO ASP GLY ALA ARG LYS LEU GLY MET GLU
                400                 405                 410                 415

GGA TGC AGC AAT GTA ACA AGC AGT GAC GAA GTG CTC TTC AAT GTA ACA GTG ACA ATG GAA AAA TGC
GLY CYS SER ASN VAL THR SER SER ASP GLU VAL LEU PHE ASN VAL THR VAL THR MET GLU LYS CYS
        420                 425                 430                 435
```

FIG. 1C

```
AGT GTC ACA GGA GGG AAG AAC TAT GCA ATA ATC AAA CCT ATT GGT TTC AAT GAA ACC AGT AAA ATC
SER VAL THR GLY GLY LYS ASN TYR ALA ILE ILE LYS PRO ILE GLY PHE ASN GLU THR SER LYS ILE
440                 445                 450                 455                 460

CAT ATA CAC CAA AAC TGT GGC TGT GAG TGT GAG GCC AGC AGA GGA GGT GCA GCG AAG TGT GCC GAG
HIS ILE HIS GLN ASN CYS GLY CYS GLU CYS GLU ALA SER ARG GLY GLY ALA ALA LYS CYS ALA GLU
            465                 470                 475                 480

GAA GCA CCC CTG GAT TCC ACG TGT CCC CAG TGC CAG GAG AGT CAG TGT CAT CAA GAG GAA GCA CAA
GLU ALA PRO LEU ASP SER THR CYS PRO GLN CYS GLN GLU SER GLN CYS HIS GLN GLU GLU ALA GLN
    485                 490                 495                 500                 505

TCT CCC AGT CAG GGC TGC AAG GCC CAC GAG GAC CAA CCG GTG TGC AGT GGC CGA GGG GTT TGC GTT
SER PRO SER GLN GLY CYS LYS ALA HIS GLU ASP GLN PRO VAL CYS SER GLY ARG GLY VAL CYS VAL
                510                 515                 520                 525

TGT GGG AAA TGC CTA TGT CAC AAG ATG AAG CTT GGA AAA GTG TAT GGA AAA TAC TGT GAA AAA GAT
CYS GLY LYS CYS LEU CYS HIS LYS MET LYS LEU GLY LYS VAL TYR GLY LYS TYR CYS GLU LYS ASP
        530                 535                 540                 545

GAC TTT TCC TGT CCC TAT CAT CAT GGC AGT CTG TGT GCT GGG CAC GGA GAG TGT GAA GCG GGC AGA
ASP PHE SER CYS PRO TYR HIS HIS GLY SER LEU CYS ALA GLY HIS GLY GLU CYS GLU ALA GLY ARG
550                 555                 560                 565                 570

TGC CAA TGC TTC AGT GGC TGG GAA GGG GAT CGG TGC CAG TGC CCG TCA GCA GCA GCC CAG CAC TGT
CYS GLN CYS PHE SER GLY TRP GLU GLY ASP ARG CYS GLN CYS PRO SER ALA ALA ALA GLN HIS CYS
            575                 580                 585                 590
GTC AAT TCC AAG GGC CAA GTG TGC AGC GGA AGA GGC ACG TGT GTG TGT GGC AGG TGC GAG TGC AGC
VAL ASN SER LYS GLY GLN VAL CYS SER GLY ARG GLY THR CYS VAL CYS GLY ARG CYS GLU CYS SER
    595                 600                 605                 610                 615
```

FIG. 1D

```
GAT CCC AGG AGC ATC GGT CGC TTC TGT GAA CAC TGT CCC ACA TGT CCT ACA GCC TGC AGT GAA AAC
ASP PRO ARG SER ILE GLY ARG PHE CYS GLU HIS CYS PRO THR CYS PRO THR ALA CYS SER GLU ASN
                620                 625                 630                 635

TGG AAT TGT GTG CAA TGC CTT CAC CCT CAC AAT CTG TCC CAG GCT ATA CTT GAT CAG TGT AGA ACC
TRP ASN CYS VAL GLN CYS LEU HIS PRO HIS ASN LEU SER GLN ALA ILE LEU ASP GLN CYS ARG THR
        640                 645                 650                 655

TCA TGT GCT TCC ATG GAG CAG CCT TAT GTG GAG CAG GCA TCA GAG TGT TTC TCT AGC CCA AGC TAC
SER CYS ALA SER MET GLU GLN PRO TYR VAL GLU GLN ALA SER GLU CYS PHE SER SER PRO SER TYR
660                 665                 670                 675                 680

TTG AGG ATT TTT TTC ATC ATA TTC ATA GTC ACG TTC TTG ATT GGG TTG CTT AAA ATC CTG ATC ATT
LEU ARG ILE PHE PHE ILE ILE PHE ILE VAL THR PHE LEU ILE GLY LEU LEU LYS ILE LEU ILE ILE
            685                 690                 695                 700

AGA CAA GTG ATA CTA CAA TGG AAT AGC AGT AAA ATC AAG TCC TCC TCA GAT TAC AGA GTG TCA GCC
ARG GLN VAL ILE LEU GLN TRP ASN SER SER LYS ILE LYS SER SER SER ASP TYR ARG VAL SER ALA
    705                 710                 715                 720                 725

TCA AAA AAG GAT AAG CTG ATT CTG CAG AGT GTT TGC ACA AGA GCA GTG ACC TAC CGA CGT GAG AAA
SER LYS LYS ASP LYS LEU ILE LEU GLN SER VAL CYS THR ARG ALA VAL THR TYR ARG ARG GLU LYS
                730                 735                 740                 745

CCT GAA GAG ATA AAA TTG GAT ATC AGT AAA TTA AAT GCT CAT GAA ACT TTC AGG TGC AAC TTC
PRO GLU GLU ILE LYS LEU ASP ILE SER LYS LEU ASN ALA HIS GLU THR PHE ARG CYS ASN PHE
        750                 755                 760                 765         768

TAAGA AAAAAAAAA AA 2972
```

FIG. 1E

```
CCCAGAGCCG CCTCCCCCTG TTGCTGGCAT CCCGAGCTTC CTCCCTTGCC AGCCAGGACG CTGCCGACTT GTCTTTGCCC
GCTGCTCCGC AGACGGGGCT GCAAAGCTGC AACTAATGGT GTTGGCCTCC CTGCCCACCT GTGGAAGCAA CTGCGCTGAT
TGATGCGCCA CAGACTTTTT TCCCCTCGAC CTCGCCGGCG TACCCTCCCA CAGATCCAGC ATCACCCAGT GAATGTACAT
TAGGGTGGTT TCCCCCCCAG CTTCGGGCTT TGTTTGGGTT TGATTGTGTT TGGCTCTTCG CTAAGCTGAT TTATGCAGCA
GAAGCCCCAC CGGCTGGAGA GAAACAAAAG CTCTTTTCTT TGTCCCGGAG CAGGCTGCGG AGCCCTTGCA GAGCCCTCTC
TCCAGTCGCC GCCGGGCCCT TGGCCGTCGA AGGAGGTGCT TCTCGCGGAG ACCGCGGGAC CCGCCGTGCC GAGCCGGGAG
GGCCGTAGGG GCCCTGAGAT GCCGAGCGGT GCCCGGGCCC GCTTACCTGC ACCGCTTGCT CCGAGCCGCG GGGTCCGCCT
GCTAGGCCTG CGGAAAACGT CCTAGCGACA CTCGCCCGCG GGCCCCGAGG TCGCCCGGGA GGCCGAGCCC GCGTCCGGAA
GGCAGCCAGG CGGCGGGCGC GGGGCGGGCT GTTTTGCATT

ATG TGC GGC TCG GCC CTG GCT TTT TTT ACC GCT GCA TTT GTC TGC CTG CAA AAC GAC CGG CGA
MET CYS GLY SER ALA LEU ALA PHE PHE THR ALA ALA PHE VAL CYS LEU GLN ASN ASP ARG ARG
 1               5                  10                  15                  20

GGT CCC GCC TCG TTC CTC TGG GCA GCC TGG GTG TTT TCA CTT GTT CTT GGA CTG GGC CAA GGT
GLY PRO ALA SER PHE LEU TRP ALA ALA TRP VAL PHE SER LEU VAL LEU GLY LEU GLY GLN GLY
                25                  30                  35                  40

GAA GAC AAT AGA TGT GCA TCT TCA AAT GCA GCA TCC TGT GCC AGG TGC CTT GCG CTG GGT CCA
GLU ASP ASN ARG CYS ALA SER SER ASN ALA ALA SER CYS ALA ARG CYS LEU ALA LEU GLY PRO
        45                  50                  55                  60

GAA TGT GGA TGG TGT GTT CAA GAG GAT TTC ATT TCA GGT GGA TCA AGA AGT GAA CGT TGT GAT
GLU CYS GLY TRP CYS VAL GLN GLU ASP PHE ILE SER GLY GLY SER ARG SER GLU ARG CYS ASP
    65                  70                  75                  80
```

FIG. 2A

```
ATT GTT TCC AAT TTA ATA AGC AAA GGC TGC TCA GTT GAT TCA ATA GAA TAC CCA TCT GTG CAT
ILE VAL SER ASN LEU ILE SER LYS GLY CYS SER VAL ASP SER ILE GLU TYR PRO SER VAL HIS
 85                  90                  95                 100                 105

GTT ATA ATA CCC ACT GAA AAT GAA ATT AAT ACC CAG GTG ACA CCA GGA GAA GTG TCT ATC CAG
VAL ILE ILE PRO THR GLU ASN GLU ILE ASN THR GLN VAL THR PRO GLY GLU VAL SER ILE GLN
                110                 115                 120                 125

CTG CGT CCA GGA GCC GAA GCT AAT TTT ATG CTG AAA GTT CAT CCT CTG AAG AAA TAT CCT GTG
LEU ARG PRO GLY ALA GLU ALA ASN PHE MET LEU LYS VAL HIS PRO LEU LYS LYS TYR PRO VAL
            130                 135                 140                 145

GAT CTT TAT TAT CTT GTT GAT GTC TCA GCA TCA ATG CAC AAT AAT ATA GAA AAA TTA AAT TCC
ASP LEU TYR TYR LEU VAL ASP VAL SER ALA SER MET HIS ASN ASN ILE GLU LYS LEU ASN SER
        150                 155                 160                 165

GTT GGA AAC GAT TTA TCT AGA AAA ATG GCA TTT TTC TCC CGT GAC TTT CGT CTT GGA TTT GGC
VAL GLY ASN ASP LEU SER ARG LYS MET ALA PHE PHE SER ARG ASP PHE ARG LEU GLY PHE GLY
    170                 175                 180                 185
```

FIG. 2B

```
TCA TAC GTT GAT AAA ACA GTT TCA CCA TAC ATT AGC ATC CAC CCC GAA AGG ATT CAT AAT CAA
SER TYR VAL ASP LYS THR VAL SER PRO TYR ILE SER ILE HIS PRO GLU ARG ILE HIS ASN GLN
190                 195                 200                 205                 210

TGC AGT GAC TAC AAT TTA GAC TGC ATG CCT CCC CAT GGA TAC ATC CAT GTG CTG TCT TTG ACA
CYS SER ASP TYR ASN LEU ASP CYS MET PRO PRO HIS GLY TYR ILE HIS VAL LEU SER LEU THR
                215                 220                 225                 230

GAG AAC ATC ACT GAG TTT GAG AAA GCA GTT CAT AGA CAG AAG ATC TCT GGA AAC ATA GAT ACA
GLU ASN ILE THR GLU PHE GLU LYS ALA VAL HIS ARG GLN LYS ILE SER GLY ASN ILE ASP THR
            235                 240                 245                 250

CCA GAA GGA GGT TTT GAC GCC ATG CTT CAG GCA GCT GTC TGT GAA AGT CAT ATC GGA TGG CGA
PRO GLU GLY GLY PHE ASP ALA MET LEU GLN ALA ALA VAL CYS GLU SER HIS ILE GLY TRP ARG
        255                 260                 265                 270

AAA GAG GCT AAA AGA CTG CTG GTG ATG ACA GAT CAG ACG TCT CAT CTC GCT CTT GAT AGC AAA
LYS GLU ALA LYS ARG LEU LEU VAL MET THR ASP GLN THR SER HIS LEU ALA LEU ASP SER LYS
    275                 280                 285                 290                 295
```

FIG. 2C

```
TTG GCA GGC ATA GTG GTG CCC AAT GAC GGA AAC TGT CAT CTG AAA AAC AAC GTC TAC GTC AAA
LEU ALA GLY ILE VAL VAL PRO ASN ASP GLY ASN CYS HIS LEU LYS ASN ASN VAL TYR VAL LYS
                300                 305                 310                 315

TCG ACA ACC ATG GAA CAC CCC TCA CTA GGC CAA CTT TCA GAG AAA TTA ATA GAC AAC AAC ATT
SER THR THR MET GLU HIS PRO SER LEU GLY GLN LEU SER GLU LYS LEU ILE ASP ASN ASN ILE
            320                 325                 330                 335

AAT GTC ATC TTT GCA GTT CAA GGA AAA CAA TTT CAT TGG TAT AAG GAT CTT CTA CCC CTC TTG
ASN VAL ILE PHE ALA VAL GLN GLY LYS GLN PHE HIS TRP TYR LYS ASP LEU LEU PRO LEU LEU
        340                 345                 350                 355

CCA GGC ACC ATT GCT GGT GAA ATA GAA TCA AAG GCT GCA AAC CTC AAT AAT TTG GTA GTG GAA
PRO GLY THR ILE ALA GLY GLU ILE GLU SER LYS ALA ALA ASN LEU ASN ASN LEU VAL VAL GLU
    360                 365                 370                 375

GCC TAT CAG AAG CTC ATT TCA GAA GTG AAA GTT CAG GTG GAA AAC CAG GTA CAA GGC ATC TAT
ALA TYR GLN LYS LEU ILE SER GLU VAL LYS VAL GLN VAL GLU ASN GLN VAL GLN GLY ILE TYR
380                 385                 390                 395                 400
```

FIG. 2D

```
TTT AAC ATT ACC GCC ATC TGT CCA GAT GGG TCC AGA AAG CCA GGC ATG GAA GGA TGC AGA AAC
PHE ASN ILE THR ALA ILE CYS PRO ASP GLY SER ARG LYS PRO GLY MET GLU GLY CYS ARG ASN
                405                 410                 415                 420

GTG ACG AGC AAT GAT GAA GTT CTT TTC AAT GTA ACA GTT ACA ATG AAA AAA TGT GAT GTC ACA
VAL THR SER ASN ASP GLU VAL LEU PHE ASN VAL THR VAL THR MET LYS LYS CYS ASP VAL THR
            425                 430                 435                 440

GGA GGA AAA AAC TAT GCA ATA ATC AAA CCT ATT GGT TTT AAT GAA ACC GCT AAA ATT CAT ATA
GLY GLY LYS ASN TYR ALA ILE ILE LYS PRO ILE GLY PHE ASN GLU THR ALA LYS ILE HIS ILE
        445                 450                 455                 460

CAC AGA AAC TGC AGC TGT CAG TGT GAG GAC AAC AGA GGA CCT AAA GGA AAG TGT GTA GAT GAA
HIS ARG ASN CYS SER CYS GLN CYS GLU ASP ASN ARG GLY PRO LYS GLY LYS CYS VAL ASP GLU
    465                 470                 475                 480

ACT TTT CTA GAT TCC AAG TGT TTC CAG TGT GAT GAG AAT AAA TGT CAT TTT GAT GAA GAT CAG
THR PHE LEU ASP SER LYS CYS PHE GLN CYS ASP GLU ASN LYS CYS HIS PHE ASP GLU ASP GLN
485                 490                 495                 500                 505
```

FIG. 2E

```
TTT TCT TCT GAG AGT TGC AAG TCA CAC AAG GAT CAG CCT GTT TGC AGT GGT CGA GGA GTT TGT
PHE SER SER GLU SER CYS LYS SER HIS LYS ASP GLN PRO VAL CYS SER GLY ARG GLY VAL CYS
                510                 515                 520                 525

GTT TGT GGG AAA TGT TCA TGT CAC AAA ATT AAG CTT GGA AAA GTG TAT GGA AAA TAC TGT GAA
VAL CYS GLY LYS CYS SER CYS HIS LYS ILE LYS LEU GLY LYS VAL TYR GLY LYS TYR CYS GLU
            530                 535                 540                 545

AAG GAT GAC TTT TCT TGT CCA TAT CAC CAT GGA AAT CTG TGT GCT GGG CAT GGA GAG TGT GAA
LYS ASP ASP PHE SER CYS PRO TYR HIS HIS GLY ASN LEU CYS ALA GLY HIS GLY GLU CYS GLU
        550                 555                 560                 565

GCA GGC AGA TGC CAA TGC TTC AGT GGC TGG GAA GGT GAT CGA TGC CAG TGC CCT TCA GCA GCA
ALA GLY ARG CYS GLN CYS PHE SER GLY TRP GLU GLY ASP ARG CYS GLN CYS PRO SER ALA ALA
    570                 575                 580                 585

GCC CAG CAC TGT GTC AAT TCA AAG GGC CAA GTG TGC AGT GGA AGA GGC ACG TGT GTG TGT GGA
ALA GLN HIS CYS VAL ASN SER LYS GLY GLN VAL CYS SER GLY ARG GLY THR CYS VAL CYS GLY
590                 595                 600                 605                 610
```

FIG. 2F

```
AGG TGT GAG TGC ACC GAT CCC AGG AGC ATC GGC CGC TTC TGT GAA CAC TGC CCC ACC TGT TAT
ARG CYS GLU CYS THR ASP PRO ARG SER ILE GLY ARG PHE CYS GLU HIS CYS PRO THR CYS TYR
                615                 620                 625                 630

ACA GCC TGC AAG GAA AAC TGG AAT TGT ATG CAA TGC CTT CAC CCT CAC AAT TTG TCT CAG GCT
THR ALA CYS LYS GLU ASN TRP ASN CYS MET GLN CYS LEU HIS PRO HIS ASN LEU SER GLN ALA
            635                 640                 645                 650

ATA CTT GAT CAG TGC AAA ACC TCA TGT GCT CTC ATG GAA CAA CAG CAT TAT GTC GAC CAA ACT
ILE LEU ASP GLN CYS LYS THR SER CYS ALA LEU MET GLU GLN GLN HIS TYR VAL ASP GLN THR
        655                 660                 665                 670

TCA GAA TGT TTC TCC AGC CCA AGC TAC TTG AGA ATA TTT TTC ATC ATT TTC ATA GTT ACA TTC
SER GLU CYS PHE SER SER PRO SER TYR LEU ARG ILE PHE PHE ILE ILE PHE ILE VAL THR PHE
    675                 680                 685                 690

TTG ATT GGG TTG CTT AAA GTC CTG ATC ATT AGA CAG GTG ATA CTA CAA TGG AAT AGT AAT AAA
LEU ILE GLY LEU LEU LYS VAL LEU ILE ILE ARG GLN VAL ILE LEU GLN TRP ASN SER ASN LYS
695                 700                 705                 710                 715
```

FIG. 2G

```
ATT AAG TCC TCA TCA GAT TAC AGA GTG TCA GCC TCA AAA AAG GAT AAG TTG ATT CTG CAA AGT
ILE LYS SER SER SER ASP TYR ARG VAL SER ALA SER LYS LYS ASP LYS LEU ILE LEU GLN SER
                720                 725                 730                 735

GTT TGC ACA AGA GCA GTC ACC TAC CGA CGT GAG AAG CCT GAA GAA ATA AAA ATG GAT ATC AGC
VAL CYS THR ARG ALA VAL THR TYR ARG ARG GLU LYS PRO GLU GLU ILE LYS MET ASP ILE SER
            740                 745                 750                 755

AAA TTA AAT GCT CAT GAA ACT TTC AGG TGC AAC TTC TAA 2990
LYS LEU ASN ALA HIS GLU THR PHE ARG CYS ASN PHE
        760                 765             769

AAAAAGATTT TTAAACACTT AATGGGAAAC TGGAATTGTT AATAATTGCT CCTAAAGATT ATAATTTTAA AAGTCACAGG

AGGAGACAAA TTGCTCACGG TCATGCCAGT TGCTGGTTGT ACACTCGAAC GAAGACTGAC AAGTATCCTC ATCATGATGT

GACTCACATA GCTGCTGACT TTTTCAGAGA AAAATGTGTC TTACTACTGT TTGAGACTAG TGTCGTTGTA GCACTTTACT

GTAATATATA ACTTATTTAG ATCAGCATAG AATGTAGATC CTCTGAAGAG CACTGATTAC ACTTTACAGG TACCTGTTAT

CCCTACGCTT CCCAGAGAGA ACAATGCTGT GAGAGAGTTT AGCATTGTGT CACTACAAGG GTACAGTAAT CCCTGCACTG

GACATGTGAG GAAAAAAATA ATCTGGCAAG TATATTCTAA GGTTGCCAAA CACTTCAACA GTTGGTGGTT GAATAGACAA

GAACAGCTAG ATGAATAAAT GATTCGTGTT TCACTCTTTC AAGAGGTGAA CAGATACAAC CTTAATCTTA AAAGATTATT

GCTTTTTAAA GTGTGTAGTT TTATGCATGT GTGTTTATGG TTTGCTTATT TTTGCAAGAT GGATACTAAT TCCAGCATTC

TCTCCTCTTT GCCTTTATGT TTTGTTTTCT TTTTTACAGG ATAAGTTTAT GTATGTCACA GATGACTGGA TTAATTAAGT

GCTAAGTTAC TACTGCCATA AAAAACTAAT AATACAATGT CACTTTATCA GAATACTAGT TTTAAAAGCT GAATGTTAA
```

FIG. 2H

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 97 base pairs
( B ) TYPE: Nucleic Acid
( C ) STRANDEDNESS: Single
( D ) TOPOLOGY: Linear ( x i ) SEQUENCE DESCRIPTION: SEQ ID NO:1:

```
AAGCAGAGTG TGTCACGGAA CCGAGATGCC CCAGAGGGTG GCTTTGATGC 50
CATCATGCAG GCTACAGTCT GTGATGAAAA GATTGGCTGG AGGAATG 97
```

( 2 ) INFORMATION FOR SEQ ID NO:2:

( i ) SEQUENCE CHARACTERISTICS:
( A ) LENGTH: 45 base pairs
( B ) TYPE: Nucleic Acid
( C ) STRANDEDNESS: Single
( D ) TOPOLOGY: Linear ( x i ) SEQUENCE DESCRIPTION: SEQ ID NO:2:

```
ACGTGCGAGA AGTGCCCCAC CTGCCCGGAT GCTTGCAGCA CCAAG 45
```

( 2 ) INFORMATION FOR SEQ ID NO:3:

( i ) SEQUENCE CHARACTERISTICS:
( A ) LENGTH: 2972 base pairs
( B ) TYPE: Nucleic Acid
( C ) STRANDEDNESS: Single
( D ) TOPOLOGY: Linear ( x i ) SEQUENCE DESCRIPTION: SEQ ID NO:3:

```
GGCGATGGCT CGCGCGGAGC CTGCGGGCGT CGGCAGGCGC TGCTAGGGCG 50
CTCCCGGAGC CGCCTCCCCG GGCTGCTGGC GCCCAGAGCT TCCTCCCTGG 100
CCCGCCGGGC GCGGGGCTGC AAGCCGGGGG ACGTGGCCTC TCCTGCCCAC 150
CTGTGGAAGG AGCTCGCGCC GATGGCTGCG CCCTCCGGCC TCGCAGGCGT 200
CCCCTCCCAC TAAGGCAGCA TCACCCAGCG AATGTACTTT AGGGTGGTTT 250
CCCCCTCCCC AGCTTCGGGC TTTGTTTGGG TTTGATTGTG TTTGGCTCTC 300
CGCTAAGCTG ATTTATGCAG CACAAGCCCC ATCGGCTGGC GAGAAACAAA 350
AGCTCTTTTC TTTGTCCCGG GAGCGGGCTT GCGGAGCCCC GGCTCGCGTC 400
GGCGACCGGG CCATCGGCCG TCGCGGGAGG CGCTGCTGGC CGAGGCCGCG 450
```

-continued

```
CCGAGCTGGG AGGGCCGCGG GGGCCCTGGG ATGCCGAGCG GCGCCGGGGC 500

CCGCGTACCT GCACCGCCTG CCGGGGAGCG CCTGCCAGGC CTGCTGGAGA 550

CGTCCTAGCG GGCTCGGCCC GGGCCCCGAG GTCGCCCGGG AGGCCGAGCG 600

CGCGTCCCCA GAGCGGCCAG GCGGCGGGCG CGGGGCGGGC CGCTGTGCAG 650

T   ATG TGC GGC TCG GCC CTG GGT CTC CCT CCC GCC GCA 687
    Met Cys Gly Ser Ala Leu Gly Leu Pro Pro Ala Ala
     1              5                   10

TTC GTC CGC CTG CGC AGC TGC CGG CCA GGT CCT GCG GCG 726
Phe Val Arg Leu Arg Ser Cys Arg Pro Gly Pro Ala Ala
        15                  20                  25

TTC CTC CGG GCG GCC TGG GTG CTC TCA CTT GTT CTC GGA 765
Phe Leu Arg Ala Ala Trp Val Leu Ser Leu Val Leu Gly
                30                  35

CTG GGT CGA AGC GAA AAC AGT AGA TGC GCA TCC TCC CAT 804
Leu Gly Arg Ser Glu Asn Ser Arg Cys Ala Ser Ser His
    40                  45                  50

GCT GTG TCG TGT TCC GAG TGC CTT GCG CTG GGT CCA GAC 843
Ala Val Ser Cys Ser Glu Cys Leu Ala Leu Gly Pro Asp
            55                  60

TGT GGA TGG TGT GTT CAC GAG GAT TTC ATC TCA GGT GGA 882
Cys Gly Trp Cys Val His Glu Asp Phe Ile Ser Gly Gly
65                  70                  75

CCA AGG AGT GAG CGC TGT GAT ATT GTT TCC AAT TTA ATA 921
Pro Arg Ser Glu Arg Cys Asp Ile Val Ser Asn Leu Ile
        80                  85                  90

AGC AAA GGC TGC CCG GTG GAT TCA ATA GAA TAC CCA TCT 960
Ser Lys Gly Cys Pro Val Asp Ser Ile Glu Tyr Pro Ser
                95                  100

GTG CAT GTG ACA ATT CCA AGT GAA AAT GAA GTT AAT ACC 999
Val His Val Thr Ile Pro Ser Glu Asn Glu Val Asn Thr
    105                 110                 115

CAG GTG ACA CCA GGA GAA GTG TCG ATT CAG CTG CGA CCA 1038
Gln Val Thr Pro Gly Glu Val Ser Ile Gln Leu Arg Pro
            120                 125

GGA GCT GCA GCT AAT TTT ATG CTG AAA ATT CAT CCG CTG 1077
Gly Ala Ala Ala Asn Phe Met Leu Lys Ile His Pro Leu
130                 135                 140

AAG AAA TAT CCT GTG GAT CTT TAT TAT CTG GTA GAT GTC 1116
Lys Lys Tyr Pro Val Asp Leu Tyr Tyr Leu Val Asp Val
        145                 150                 155

TCA GCA TCA ATG CAC AAC AAT ATA GAA AAA TTA AAT TCT 1155
Ser Ala Ser Met His Asn Asn Ile Glu Lys Leu Asn Ser
                160                 165

GTT GGA AAT GAC TTA TCT AGA AAA ATG GCA TTT TTC TCC 1194
Val Gly Asn Asp Leu Ser Arg Lys Met Ala Phe Phe Ser
    170                 175                 180

CGT GAC TTC CGC CTT GGG TTC GGC TCC TAT GTT GAT AAA 1233
Arg Asp Phe Arg Leu Gly Phe Gly Ser Tyr Val Asp Lys
            185                 190

ACA GTC TCA CCA TAC ATC AGT ATC CAC CCA GAA AGG ATT 1272
Thr Val Ser Pro Tyr Ile Ser Ile His Pro Glu Arg Ile
195                 200                 205

CAC AAC CAA TGC AGT GAC TAC AAC TTA GAC TGC ATG CCC 1311
His Asn Gln Cys Ser Asp Tyr Asn Leu Asp Cys Met Pro
        210                 215                 220

CCC CAC GGA TAC ATC CAT GTG CTG TCC CTG ACG GAG AAC 1350
Pro His Gly Tyr Ile His Val Leu Ser Leu Thr Glu Asn
                225                 230
```

-continued

```
ATC ACG GAG TTC GAG CGA GCT GTG CAC AGA CAG AAA ATC 1389
Ile Thr Glu Phe Glu Arg Ala Val His Arg Gln Lys Ile
    235                 240                 245

TCT GGC AAC ATC GAC ACA CCC GAA GGA GGC TTT GAT GCC 1428
Ser Gly Asn Ile Asp Thr Pro Glu Gly Gly Phe Asp Ala
            250                 255

ATG CTG CAG GCT GCC GTC TGC GAG AGT CAC ATC GGA TGG 1467
Met Leu Gln Ala Ala Val Cys Glu Ser His Ile Gly Trp
260                 265                 270

CGA AAA GAA GCT AAA AGA TTG CTG CTG GTG ATG ACG GAT 1506
Arg Lys Glu Ala Lys Arg Leu Leu Leu Val Met Thr Asp
        275                 280                 285

CAG ACA TCT CAT CTG GCC CTT GAT AGC AAG TTG GCA GGC 1545
Gln Thr Ser His Leu Ala Leu Asp Ser Lys Leu Ala Gly
                290                 295

ATT GTG GTG CCG AAT GAT GGA AAT TGC CAT CTG AGA AAC 1584
Ile Val Val Pro Asn Asp Gly Asn Cys His Leu Arg Asn
    300                 305                 310

AAC GTC TAC GTC AAG TCC ACA ACC ATG GAA CAT CCC TCA 1623
Asn Val Tyr Val Lys Ser Thr Thr Met Glu His Pro Ser
            315                 320

CTA GGC CAA CTT TCA GAG AAA TTA ATA GAC AAC AAC ATC 1662
Leu Gly Gln Leu Ser Glu Lys Leu Ile Asp Asn Asn Ile
325                 330                 335

AAT GTC ATC TTT GCA GTT CAA GGA AAA CAG TTT CAT TGG 1701
Asn Val Ile Phe Ala Val Gln Gly Lys Gln Phe His Trp
        340                 345                 350

TAT AAG GAC CTT CTA CCC CTC TTG CCG GGT ACC ATT GCT 1740
Tyr Lys Asp Leu Leu Pro Leu Leu Pro Gly Thr Ile Ala
                355                 360

GGT GAA ATA GAA TCA AAG GCT GCA AAC CTC AAT AAT TTG 1779
Gly Glu Ile Glu Ser Lys Ala Ala Asn Leu Asn Asn Leu
    365                 370                 375

GTA GTA GAA GCC TAT CAG AAA CTC ATT TCA GAA GTG AAA 1818
Val Val Glu Ala Tyr Gln Lys Leu Ile Ser Glu Val Lys
            380                 385

GTG CAG GTG GAA AGC AAA GTG CCA GGC GTC TAC TTT AAC 1857
Val Gln Val Glu Ser Lys Val Pro Gly Val Tyr Phe Asn
390                 395                 400

GTC ACA GCC ATC TGT CCA GAT GGA GCC AGG AAG CTG GGC 1896
Val Thr Ala Ile Cys Pro Asp Gly Ala Arg Lys Leu Gly
        405                 410                 415

ATG GAA GGA TGC AGC AAT GTA ACA AGC AGT GAC GAA GTG 1935
Met Glu Gly Cys Ser Asn Val Thr Ser Ser Asp Glu Val
                420                 425

CTC TTC AAT GTA ACA GTG ACA ATG GAA AAA TGC AGT GTC 1974
Leu Phe Asn Val Thr Val Thr Met Glu Lys Cys Ser Val
    430                 435                 440

ACA GGA GGG AAG AAC TAT GCA ATA ATC AAA CCT ATT GGT 2013
Thr Gly Gly Lys Asn Tyr Ala Ile Ile Lys Pro Ile Gly
            445                 450

TTC AAT GAA ACC AGT AAA ATC CAT ATA CAC CAA AAC TGT 2052
Phe Asn Glu Thr Ser Lys Ile His Ile His Gln Asn Cys
455                 460                 465

GGC TGT GAG TGT GAG GCC AGC AGA GGA GGT GCA GCG AAG 2091
Gly Cys Glu Cys Glu Ala Ser Arg Gly Gly Ala Ala Lys
        470                 475                 480

TGT GCC GAG GAA GCA CCC CTG GAT TCC ACG TGT CCC CAG 2130
Cys Ala Glu Glu Ala Pro Leu Asp Ser Thr Cys Pro Gln
                485                 490
```

```
TGC CAG GAG AGT CAG TGT CAT CAA GAG GAA GCA CAA TCT 2169
Cys Gln Glu Ser Gln Cys His Gln Glu Glu Ala Gln Ser
    495                 500                 505

CCC AGT CAG GGC TGC AAG GCC CAC GAG GAC CAA CCG GTG 2208
Pro Ser Gln Gly Cys Lys Ala His Glu Asp Gln Pro Val
            510                 515

TGC AGT GGC CGA GGG GTT TGC GTT TGT GGG AAA TGC CTA 2247
Cys Ser Gly Arg Gly Val Cys Val Cys Gly Lys Cys Leu
520                 525                 530

TGT CAC AAG ATG AAG CTT GGA AAA GTG TAT GGA AAA TAC 2286
Cys His Lys Met Lys Leu Gly Lys Val Tyr Gly Lys Tyr
        535                 540                 545

TGT GAA AAA GAT GAC TTT TCC TGT CCC TAT CAT CAT GGC 2325
Cys Glu Lys Asp Asp Phe Ser Cys Pro Tyr His His Gly
                550                 555

AGT CTG TGT GCT GGG CAC GGA GAG TGT GAA GCG GGC AGA 2364
Ser Leu Cys Ala Gly His Gly Glu Cys Glu Ala Gly Arg
    560                 565                 570

TGC CAA TGC TTC AGT GGC TGG GAA GGG GAT CGG TGC CAG 2403
Cys Gln Cys Phe Ser Gly Trp Glu Gly Asp Arg Cys Gln
            575                 580

TGC CCG TCA GCA GCA GCC CAG CAC TGT GTC AAT TCC AAG 2442
Cys Pro Ser Ala Ala Ala Gln His Cys Val Asn Ser Lys
585                 590                 595

GGC CAA GTG TGC AGC GGA AGA GGC ACG TGT GTG TGT GGC 2481
Gly Gln Val Cys Ser Gly Arg Gly Thr Cys Val Cys Gly
        600                 605                 610

AGG TGC GAG TGC AGC GAT CCC AGG AGC ATC GGT CGC TTC 2520
Arg Cys Glu Cys Ser Asp Pro Arg Ser Ile Gly Arg Phe
                615                 620

TGT GAA CAC TGT CCC ACA TGT CCT ACA GCC TGC AGT GAA 2559
Cys Glu His Cys Pro Thr Cys Pro Thr Ala Cys Ser Glu
    625                 630                 635

AAC TGG AAT TGT GTG CAA TGC CTT CAC CCT CAC AAT CTG 2598
Asn Trp Asn Cys Val Gln Cys Leu His Pro His Asn Leu
            640                 645

TCC CAG GCT ATA CTT GAT CAG TGT AGA ACC TCA TGT GCT 2637
Ser Gln Ala Ile Leu Asp Gln Cys Arg Thr Ser Cys Ala
650                 655                 660

TCC ATG GAG CAG CCT TAT GTG GAG CAG GCA TCA GAG TGT 2676
Ser Met Glu Gln Pro Tyr Val Glu Gln Ala Ser Glu Cys
        665                 670                 675

TTC TCT AGC CCA AGC TAC TTG AGG ATT TTT TTC ATC ATA 2715
Phe Ser Ser Pro Ser Tyr Leu Arg Ile Phe Phe Ile Ile
                680                 685

TTC ATA GTC ACG TTC TTG ATT GGG TTG CTT AAA ATC CTG 2754
Phe Ile Val Thr Phe Leu Ile Gly Leu Leu Lys Ile Leu
    690                 695                 700

ATC ATT AGA CAA GTG ATA CTA CAA TGG AAT AGC AGT AAA 2793
Ile Ile Arg Gln Val Ile Leu Gln Trp Asn Ser Ser Lys
            705                 710

ATC AAG TCC TCC TCA GAT TAC AGA GTG TCA GCC TCA AAA 2832
Ile Lys Ser Ser Ser Asp Tyr Arg Val Ser Ala Ser Lys
715                 720                 725

AAG GAT AAG CTG ATT CTG CAG AGT GTT TGC ACA AGA GCA 2871
Lys Asp Lys Leu Ile Leu Gln Ser Val Cys Thr Arg Ala
        730                 735                 740

GTG ACC TAC CGA CGT GAG AAA CCT GAA GAG ATA AAA TTG 2910
Val Thr Tyr Arg Arg Glu Lys Pro Glu Glu Ile Lys Leu
                745                 750
```

```
GAT ATC AGT AAA TTA AAT GCT CAT GAA ACT TTC AGG TGC 2949
Asp Ile Ser Lys Leu Asn Ala His Glu Thr Phe Arg Cys
    755                 760                 765

AAC TTC TAAGA AAAAAAAAA AA 2972
Asn Phe
    768
```

( 2 ) INFORMATION FOR SEQ ID NO:4:

( i ) SEQUENCE CHARACTERISTICS:
( A ) LENGTH: 768 amino acids
( B ) TYPE: Amino Acid
( D ) TOPOLOGY: Linear ( x i ) SEQUENCE DESCRIPTION: SEQ ID NO:4:

```
Met Cys Gly Ser Ala Leu Gly Leu Pro Pro Ala Ala Phe Val Arg
  1             5                  10                  15

Leu Arg Ser Cys Arg Pro Gly Pro Ala Ala Phe Leu Arg Ala Ala
               20                  25                  30

Trp Val Leu Ser Leu Val Leu Gly Leu Gly Arg Ser Glu Asn Ser
               35                  40                  45

Arg Cys Ala Ser Ser His Ala Val Ser Cys Ser Glu Cys Leu Ala
               50                  55                  60

Leu Gly Pro Asp Cys Gly Trp Cys Val His Glu Asp Phe Ile Ser
               65                  70                  75

Gly Gly Pro Arg Ser Glu Arg Cys Asp Ile Val Ser Asn Leu Ile
               80                  85                  90

Ser Lys Gly Cys Pro Val Asp Ser Ile Glu Tyr Pro Ser Val His
               95                 100                 105

Val Thr Ile Pro Ser Glu Asn Glu Val Asn Thr Gln Val Thr Pro
              110                 115                 120

Gly Glu Val Ser Ile Gln Leu Arg Pro Gly Ala Ala Ala Asn Phe
              125                 130                 135

Met Leu Lys Ile His Pro Leu Lys Lys Tyr Pro Val Asp Leu Tyr
              140                 145                 150

Tyr Leu Val Asp Val Ser Ala Ser Met His Asn Asn Ile Glu Lys
              155                 160                 165

Leu Asn Ser Val Gly Asn Asp Leu Ser Arg Lys Met Ala Phe Phe
              170                 175                 180

Ser Arg Asp Phe Arg Leu Gly Phe Gly Ser Tyr Val Asp Lys Thr
              185                 190                 195

Val Ser Pro Tyr Ile Ser Ile His Pro Glu Arg Ile His Asn Gln
              200                 205                 210

Cys Ser Asp Tyr Asn Leu Asp Cys Met Pro Pro His Gly Tyr Ile
              215                 220                 225

His Val Leu Ser Leu Thr Glu Asn Ile Thr Glu Phe Glu Arg Ala
              230                 235                 240

Val His Arg Gln Lys Ile Ser Gly Asn Ile Asp Thr Pro Glu Gly
              245                 250                 255

Gly Phe Asp Ala Met Leu Gln Ala Ala Val Cys Glu Ser His Ile
              260                 265                 270

Gly Trp Arg Lys Glu Ala Lys Arg Leu Leu Leu Val Met Thr Asp
              275                 280                 285

Gln Thr Ser His Leu Ala Leu Asp Ser Lys Leu Ala Gly Ile Val
              290                 295                 300

Val Pro Asn Asp Gly Asn Cys His Leu Arg Asn Asn Val Tyr Val
```

-continued

```
                                305                       310                       315

Lys Ser Thr Thr Met Glu His Pro Ser Leu Gly Gln Leu Ser Glu
                320                 325                     330

Lys Leu Ile Asp Asn Asn Ile Asn Val Ile Phe Ala Val Gln Gly
                335                 340                     345

Lys Gln Phe His Trp Tyr Lys Asp Leu Leu Pro Leu Leu Pro Gly
                350                 355                     360

Thr Ile Ala Gly Glu Ile Glu Ser Lys Ala Ala Asn Leu Asn Asn
                365                 370                     375

Leu Val Val Glu Ala Tyr Gln Lys Leu Ile Ser Glu Val Lys Val
                380                 385                     390

Gln Val Glu Ser Lys Val Pro Gly Val Tyr Phe Asn Val Thr Ala
                395                 400                     405

Ile Cys Pro Asp Gly Ala Arg Lys Leu Gly Met Glu Gly Cys Ser
                410                 415                     420

Asn Val Thr Ser Ser Asp Glu Val Leu Phe Asn Val Thr Val Thr
                425                 430                     435

Met Glu Lys Cys Ser Val Thr Gly Gly Lys Asn Tyr Ala Ile Ile
                440                 445                     450

Lys Pro Ile Gly Phe Asn Glu Thr Ser Lys Ile His Ile His Gln
                455                 460                     465

Asn Cys Gly Cys Glu Cys Glu Ala Ser Arg Gly Gly Ala Ala Lys
                470                 475                     480

Cys Ala Glu Glu Ala Pro Leu Asp Ser Thr Cys Pro Gln Cys Gln
                485                 490                     495

Glu Ser Gln Cys His Gln Glu Glu Ala Gln Ser Pro Ser Gln Gly
                500                 505                     510

Cys Lys Ala His Glu Asp Gln Pro Val Cys Ser Gly Arg Gly Val
                515                 520                     525

Cys Val Cys Gly Lys Cys Leu Cys His Lys Met Lys Leu Gly Lys
                530                 535                     540

Val Tyr Gly Lys Tyr Cys Glu Lys Asp Asp Phe Ser Cys Pro Tyr
                545                 550                     555

His His Gly Ser Leu Cys Ala Gly His Gly Glu Cys Glu Ala Gly
                560                 565                     570

Arg Cys Gln Cys Phe Ser Gly Trp Glu Gly Asp Arg Cys Gln Cys
                575                 580                     585

Pro Ser Ala Ala Ala Gln His Cys Val Asn Ser Lys Gly Gln Val
                590                 595                     600

Cys Ser Gly Arg Gly Thr Cys Val Cys Gly Arg Cys Glu Cys Ser
                605                 610                     615

Asp Pro Arg Ser Ile Gly Arg Phe Cys Glu His Cys Pro Thr Cys
                620                 625                     630

Pro Thr Ala Cys Ser Glu Asn Trp Asn Cys Val Gln Cys Leu His
                635                 640                     645

Pro His Asn Leu Ser Gln Ala Ile Leu Asp Gln Cys Arg Thr Ser
                650                 655                     660

Cys Ala Ser Met Glu Gln Pro Tyr Val Glu Gln Ala Ser Glu Cys
                665                 670                     675

Phe Ser Ser Pro Ser Tyr Leu Arg Ile Phe Phe Ile Ile Phe Ile
                680                 685                     690

Val Thr Phe Leu Ile Gly Leu Leu Lys Ile Leu Ile Ile Arg Gln
                695                 700                     705
```

-continued

```
Val Ile Leu Gln Trp Asn Ser Ser Lys Ile Lys Ser Ser Ser Asp
                710                     715                 720

Tyr Arg Val Ser Ala Ser Lys Lys Asp Lys Leu Ile Leu Gln Ser
                725                     730                 735

Val Cys Thr Arg Ala Val Thr Tyr Arg Arg Glu Lys Pro Glu Glu
                740                     745                 750

Ile Lys Leu Asp Ile Ser Lys Leu Asn Ala His Glu Thr Phe Arg
                755                     760                 765

Cys Asn Phe
        768
```

( 2 ) INFORMATION FOR SEQ ID NO:5:

( i ) SEQUENCE CHARACTERISTICS:
( A ) LENGTH: 3789 base pairs
( B ) TYPE: Nucleic Acid
( C ) STRANDEDNESS: Single
( D ) TOPOLOGY: Linear ( x i ) SEQUENCE DESCRIPTION: SEQ ID NO:5:

```
CCCAGAGCCG CCTCCCCCTG TTGCTGGCAT CCCGAGCTTC CTCCCTTGCC  50

AGCCAGGACG CTGCCGACTT GTCTTTGCCC GCTGCTCCGC AGACGGGGCT 100

GCAAAGCTGC AACTAATGGT GTTGGCCTCC CTGCCCACCT GTGGAAGCAA 150

CTGCGCTGAT TGATGCGCCA CAGACTTTTT TCCCCTCGAC CTCGCCGGCG 200

TACCCTCCCA CAGATCCAGC ATCACCCAGT GAATGTACAT TAGGGTGGTT 250

TCCCCCCCAG CTTCGGGCTT TGTTTGGGTT TGATTGTGTT TGGCTCTTCG 300

CTAAGCTGAT TTATGCAGCA GAAGCCCCAC CGGCTGGAGA GAAACAAAAG 350

CTCTTTTCTT TGTCCCGGAG CAGGCTGCGG AGCCCTTGCA GAGCCCTCTC 400

TCCAGTCGCC GCCGGGCCCT TGGCCGTCGA AGGAGGTGCT TCTCGCGGAG 450

ACCGCGGGAC CCGCCGTGCC GAGCCGGGAG GGCCGTAGGG GCCCTGAGAT 500

GCCGAGCGGT GCCCGGGCCC GCTTACCTGC ACCGCTTGCT CCGAGCCGCG 550

GGGTCCGCCT GCTAGGCCTG CGGAAAACGT CCTAGCGACA CTCGCCCGCG 600

GGCCCCGAGG TCGCCCGGGA GGCCGAGCCC GCGTCCGGAA GGCAGCCAGG 650

CGGCGGGCGC GGGGCGGGCT GTTTTGCATT     ATG TGC GGC TCG 692
                                      Met Cys Gly Ser
                                        1

GCC CTG GCT TTT TTT ACC GCT GCA TTT GTC TGC CTG CAA 731
Ala Leu Ala Phe Phe Thr Ala Ala Phe Val Cys Leu Gln
  5                 10                  15

AAC GAC CGG CGA GGT CCC GCC TCG TTC CTC TGG GCA GCC 770
Asn Asp Arg Arg Gly Pro Ala Ser Phe Leu Trp Ala Ala
        20                  25                  30

TGG GTG TTT TCA CTT GTT CTT GGA CTG GGC CAA GGT GAA 809
Trp Val Phe Ser Leu Val Leu Gly Leu Gly Gln Gly Glu
                35                  40

GAC AAT AGA TGT GCA TCT TCA AAT GCA GCA TCC TGT GCC 848
Asp Asn Arg Cys Ala Ser Ser Asn Ala Ala Ser Cys Ala
     45                 50                  55

AGG TGC CTT GCG CTG GGT CCA GAA TGT GGA TGG TGT GTT 887
Arg Cys Leu Ala Leu Gly Pro Glu Cys Gly Trp Cys Val
            60                  65

CAA GAG GAT TTC ATT TCA GGT GGA TCA AGA AGT GAA CGT 926
Gln Glu Asp Phe Ile Ser Gly Gly Ser Arg Ser Glu Arg
 70                 75                  80
```

-continued

```
TGT GAT ATT GTT TCC AAT TTA ATA AGC AAA GGC TGC TCA  965
Cys Asp Ile Val Ser Asn Leu Ile Ser Lys Gly Cys Ser
         85                  90                  95

GTT GAT TCA ATA GAA TAC CCA TCT GTG CAT GTT ATA ATA 1004
Val Asp Ser Ile Glu Tyr Pro Ser Val His Val Ile Ile
                100                 105

CCC ACT GAA AAT GAA ATT AAT ACC CAG GTG ACA CCA GGA 1043
Pro Thr Glu Asn Glu Ile Asn Thr Gln Val Thr Pro Gly
    110                 115                 120

GAA GTG TCT ATC CAG CTG CGT CCA GGA GCC GAA GCT AAT 1082
Glu Val Ser Ile Gln Leu Arg Pro Gly Ala Glu Ala Asn
            125                 130

TTT ATG CTG AAA GTT CAT CCT CTG AAG AAA TAT CCT GTG 1121
Phe Met Leu Lys Val His Pro Leu Lys Lys Tyr Pro Val
135                 140                 145

GAT CTT TAT TAT CTT GTT GAT GTC TCA GCA TCA ATG CAC 1160
Asp Leu Tyr Tyr Leu Val Asp Val Ser Ala Ser Met His
        150                 155                 160

AAT AAT ATA GAA AAA TTA AAT TCC GTT GGA AAC GAT TTA 1199
Asn Asn Ile Glu Lys Leu Asn Ser Val Gly Asn Asp Leu
                165                 170

TCT AGA AAA ATG GCA TTT TTC TCC CGT GAC TTT CGT CTT 1238
Ser Arg Lys Met Ala Phe Phe Ser Arg Asp Phe Arg Leu
    175                 180                 185

GGA TTT GGC TCA TAC GTT GAT AAA ACA GTT TCA CCA TAC 1277
Gly Phe Gly Ser Tyr Val Asp Lys Thr Val Ser Pro Tyr
            190                 195

ATT AGC ATC CAC CCC GAA AGG ATT CAT AAT CAA TGC AGT 1316
Ile Ser Ile His Pro Glu Arg Ile His Asn Gln Cys Ser
200                 205                 210

GAC TAC AAT TTA GAC TGC ATG CCT CCC CAT GGA TAC ATC 1355
Asp Tyr Asn Leu Asp Cys Met Pro Pro His Gly Tyr Ile
        215                 220                 225

CAT GTG CTG TCT TTG ACA GAG AAC ATC ACT GAG TTT GAG 1394
His Val Leu Ser Leu Thr Glu Asn Ile Thr Glu Phe Glu
                230                 235

AAA GCA GTT CAT AGA CAG AAG ATC TCT GGA AAC ATA GAT 1433
Lys Ala Val His Arg Gln Lys Ile Ser Gly Asn Ile Asp
    240                 245                 250

ACA CCA GAA GGA GGT TTT GAC GCC ATG CTT CAG GCA GCT 1472
Thr Pro Glu Gly Gly Phe Asp Ala Met Leu Gln Ala Ala
            255                 260

GTC TGT GAA AGT CAT ATC GGA TGG CGA AAA GAG GCT AAA 1511
Val Cys Glu Ser His Ile Gly Trp Arg Lys Glu Ala Lys
265                 270                 275

AGA TTG CTG CTG GTG ATG ACA GAT CAG ACG TCT CAT CTC 1550
Arg Leu Leu Leu Val Met Thr Asp Gln Thr Ser His Leu
        280                 285                 290

GCT CTT GAT AGC AAA TTG GCA GGC ATA GTG GTG CCC AAT 1589
Ala Leu Asp Ser Lys Leu Ala Gly Ile Val Val Pro Asn
                295                 300

GAC GGA AAC TGT CAT CTG AAA AAC AAC GTC TAC GTC AAA 1628
Asp Gly Asn Cys His Leu Lys Asn Asn Val Tyr Val Lys
    305                 310                 315

TCG ACA ACC ATG GAA CAC CCC TCA CTA GGC CAA CTT TCA 1667
Ser Thr Thr Met Glu His Pro Ser Leu Gly Gln Leu Ser
            320                 325

GAG AAA TTA ATA GAC AAC AAC ATT AAT GTC ATC TTT GCA 1706
Glu Lys Leu Ile Asp Asn Asn Ile Asn Val Ile Phe Ala
330                 335                 340
```

-continued

```
GTT CAA GGA AAA CAA TTT CAT TGG TAT AAG GAT CTT CTA 1745
Val Gln Gly Lys Gln Phe His Trp Tyr Lys Asp Leu Leu
        345                 350                 355

CCC CTC TTG CCA GGC ACC ATT GCT GGT GAA ATA GAA TCA 1784
Pro Leu Leu Pro Gly Thr Ile Ala Gly Glu Ile Glu Ser
                360                 365

AAG GCT GCA AAC CTC AAT AAT TTG GTA GTG GAA GCC TAT 1823
Lys Ala Ala Asn Leu Asn Asn Leu Val Val Glu Ala Tyr
    370                 375                 380

CAG AAG CTC ATT TCA GAA GTG AAA GTT CAG GTG GAA AAC 1862
Gln Lys Leu Ile Ser Glu Val Lys Val Gln Val Glu Asn
            385                 390

CAG GTA CAA GGC ATC TAT TTT AAC ATT ACC GCC ATC TGT 1901
Gln Val Gln Gly Ile Tyr Phe Asn Ile Thr Ala Ile Cys
395                 400                 405

CCA GAT GGG TCC AGA AAG CCA GGC ATG GAA GGA TGC AGA 1940
Pro Asp Gly Ser Arg Lys Pro Gly Met Glu Gly Cys Arg
        410                 415                 420

AAC GTG ACG AGC AAT GAT GAA GTT CTT TTC AAT GTA ACA 1979
Asn Val Thr Ser Asn Asp Glu Val Leu Phe Asn Val Thr
                425                 430

GTT ACA ATG AAA AAA TGT GAT GTC ACA GGA GGA AAA AAC 2018
Val Thr Met Lys Lys Cys Asp Val Thr Gly Gly Lys Asn
    435                 440                 445

TAT GCA ATA ATC AAA CCT ATT GGT TTT AAT GAA ACC GCT 2057
Tyr Ala Ile Ile Lys Pro Ile Gly Phe Asn Glu Thr Ala
            450                 455

AAA ATT CAT ATA CAC AGA AAC TGC AGC TGT CAG TGT GAG 2096
Lys Ile His Ile His Arg Asn Cys Ser Cys Gln Cys Glu
460                 465                 470

GAC AAC AGA GGA CCT AAA GGA AAG TGT GTA GAT GAA ACT 2135
Asp Asn Arg Gly Pro Lys Gly Lys Cys Val Asp Glu Thr
        475                 480                 485

TTT CTA GAT TCC AAG TGT TTC CAG TGT GAT GAG AAT AAA 2174
Phe Leu Asp Ser Lys Cys Phe Gln Cys Asp Glu Asn Lys
                490                 495

TGT CAT TTT GAT GAA GAT CAG TTT TCT TCT GAG AGT TGC 2213
Cys His Phe Asp Glu Asp Gln Phe Ser Ser Glu Ser Cys
    500                 505                 510

AAG TCA CAC AAG GAT CAG CCT GTT TGC AGT GGT CGA GGA 2252
Lys Ser His Lys Asp Gln Pro Val Cys Ser Gly Arg Gly
            515                 520

GTT TGT GTT TGT GGG AAA TGT TCA TGT CAC AAA ATT AAG 2291
Val Cys Val Cys Gly Lys Cys Ser Cys His Lys Ile Lys
525                 530                 535

CTT GGA AAA GTG TAT GGA AAA TAC TGT GAA AAG GAT GAC 2330
Leu Gly Lys Val Tyr Gly Lys Tyr Cys Glu Lys Asp Asp
        540                 545                 550

TTT TCT TGT CCA TAT CAC CAT GGA AAT CTG TGT GCT GGG 2369
Phe Ser Cys Pro Tyr His His Gly Asn Leu Cys Ala Gly
                555                 560

CAT GGA GAG TGT GAA GCA GGC AGA TGC CAA TGC TTC AGT 2408
His Gly Glu Cys Glu Ala Gly Arg Cys Gln Cys Phe Ser
    565                 570                 575

GGC TGG GAA GGT GAT CGA TGC CAG TGC CCT TCA GCA GCA 2447
Gly Trp Glu Gly Asp Arg Cys Gln Cys Pro Ser Ala Ala
            580                 585

GCC CAG CAC TGT GTC AAT TCA AAG GGC CAA GTG TGC AGT 2486
Ala Gln His Cys Val Asn Ser Lys Gly Gln Val Cys Ser
590                 595                 600
```

```
GGA AGA GGC ACG TGT GTG TGT GGA AGG TGT GAG TGC ACC 2525
Gly Arg Gly Thr Cys Val Cys Gly Arg Cys Glu Cys Thr
        605                 610                 615

GAT CCC AGG AGC ATC GGC CGC TTC TGT GAA CAC TGC CCC 2564
Asp Pro Arg Ser Ile Gly Arg Phe Cys Glu His Cys Pro
                620                 625

ACC TGT TAT ACA GCC TGC AAG GAA AAC TGG AAT TGT ATG 2603
Thr Cys Tyr Thr Ala Cys Lys Glu Asn Trp Asn Cys Met
    630                 635                 640

CAA TGC CTT CAC CCT CAC AAT TTG TCT CAG GCT ATA CTT 2642
Gln Cys Leu His Pro His Asn Leu Ser Gln Ala Ile Leu
            645                 650

GAT CAG TGC AAA ACC TCA TGT GCT CTC ATG GAA CAA CAG 2681
Asp Gln Cys Lys Thr Ser Cys Ala Leu Met Glu Gln Gln
655                 660                 665

CAT TAT GTC GAC CAA ACT TCA GAA TGT TTC TCC AGC CCA 2720
His Tyr Val Asp Gln Thr Ser Glu Cys Phe Ser Ser Pro
        670                 675                 680

AGC TAC TTG AGA ATA TTT TTC ATC ATT TTC ATA GTT ACA 2759
Ser Tyr Leu Arg Ile Phe Phe Ile Ile Phe Ile Val Thr
                685                 690

TTC TTG ATT GGG TTG CTT AAA GTC CTG ATC ATT AGA CAG 2798
Phe Leu Ile Gly Leu Leu Lys Val Leu Ile Ile Arg Gln
    695                 700                 705

GTG ATA CTA CAA TGG AAT AGT AAT AAA ATT AAG TCC TCA 2837
Val Ile Leu Gln Trp Asn Ser Asn Lys Ile Lys Ser Ser
            710                 715

TCA GAT TAC AGA GTG TCA GCC TCA AAA AAG GAT AAG TTG 2876
Ser Asp Tyr Arg Val Ser Ala Ser Lys Lys Asp Lys Leu
720                 725                 730

ATT CTG CAA AGT GTT TGC ACA AGA GCA GTC ACC TAC CGA 2915
Ile Leu Gln Ser Val Cys Thr Arg Ala Val Thr Tyr Arg
        735                 740                 745

CGT GAG AAG CCT GAA GAA ATA AAA ATG GAT ATC AGC AAA 2954
Arg Glu Lys Pro Glu Glu Ile Lys Met Asp Ile Ser Lys
                750                 755

TTA AAT GCT CAT GAA ACT TTC AGG TGC AAC TTC TAA 2990
Leu Asn Ala His Glu Thr Phe Arg Cys Asn Phe
    760                 765         769

AAAAAGATTT TTAAACACTT AATGGGAAAC TGGAATTGTT AATAATTGCT 3040

CCTAAAGATT ATAATTTTAA AAGTCACAGG AGGAGACAAA TTGCTCACGG 3090

TCATGCCAGT TGCTGGTTGT ACACTCGAAC GAAGACTGAC AAGTATCCTC 3140

ATCATGATGT GACTCACATA GCTGCTGACT TTTTCAGAGA AAAATGTGTC 3190

TTACTACTGT TTGAGACTAG TGTCGTTGTA GCACTTTACT GTAATATATA 3240

ACTTATTTAG ATCAGCATAG AATGTAGATC CTCTGAAGAG CACTGATTAC 3290

ACTTTACAGG TACCTGTTAT CCCTACGCTT CCCAGAGAGA ACAATGCTGT 3340

GAGAGAGTTT AGCATTGTGT CACTACAAGG GTACAGTAAT CCCTGCACTG 3390

GACATGTGAG GAAAAAAATA ATCTGGCAAG TATATTCTAA GGTTGCCAAA 3440

CACTTCAACA GTTGGTGGTT GAATAGACAA GAACAGCTAG ATGAATAAAT 3490

GATTCGTGTT TCACTCTTTC AAGAGGTGAA CAGATACAAC CTTAATCTTA 3540

AAAGATTATT GCTTTTTAAA GTGTGTAGTT TTATGCATGT GTGTTTATGG 3590

TTTGCTTATT TTTGCAAGAT GGATACTAAT TCCAGCATTC TCTCCTCTTT 3640

GCCTTTATGT TTTGTTTTCT TTTTTACAGG ATAAGTTTAT GTATGTCACA 3690
```

GATGACTGGA TTAATTAAGT GCTAAGTTAC TACTGCCATA AAAAACTAAT 3740

AATACAATGT CACTTTATCA GAATACTAGT TTTAAAAGCT GAATGTTAA 3789

( 2 ) INFORMATION FOR SEQ ID NO:6:

( i ) SEQUENCE CHARACTERISTICS:
( A ) LENGTH: 769 amino acids
( B ) TYPE: Amino Acid
( D ) TOPOLOGY: Linear ( x i ) SEQUENCE DESCRIPTION: SEQ ID NO:6:

Met Cys Gly Ser Ala Leu Ala Phe Phe Thr Ala Ala Phe Val Cys
1 5 10 15

Leu Gln Asn Asp Arg Arg Gly Pro Ala Ser Phe Leu Trp Ala Ala
20 25 30

Trp Val Phe Ser Leu Val Leu Gly Leu Gly Gln Gly Glu Asp Asn
35 40 45

Arg Cys Ala Ser Ser Asn Ala Ala Ser Cys Ala Arg Cys Leu Ala
50 55 60

Leu Gly Pro Glu Cys Gly Trp Cys Val Gln Glu Asp Phe Ile Ser
65 70 75

Gly Gly Ser Arg Ser Glu Arg Cys Asp Ile Val Ser Asn Leu Ile
80 85 90

Ser Lys Gly Cys Ser Val Asp Ser Ile Glu Tyr Pro Ser Val His
95 100 105

Val Ile Ile Pro Thr Glu Asn Glu Ile Asn Thr Gln Val Thr Pro
110 115 120

Gly Glu Val Ser Ile Gln Leu Arg Pro Gly Ala Glu Ala Asn Phe
125 130 135

Met Leu Lys Val His Pro Leu Lys Lys Tyr Pro Val Asp Leu Tyr
140 145 150

Tyr Leu Val Asp Val Ser Ala Ser Met His Asn Asn Ile Glu Lys
155 160 165

Leu Asn Ser Val Gly Asn Asp Leu Ser Arg Lys Met Ala Phe Phe
170 175 180

Ser Arg Asp Phe Arg Leu Gly Phe Gly Ser Tyr Val Asp Lys Thr
185 190 195

Val Ser Pro Tyr Ile Ser Ile His Pro Glu Arg Ile His Asn Gln
200 205 210

Cys Ser Asp Tyr Asn Leu Asp Cys Met Pro Pro His Gly Tyr Ile
215 220 225

His Val Leu Ser Leu Thr Glu Asn Ile Thr Glu Phe Glu Lys Ala
230 235 240

Val His Arg Gln Lys Ile Ser Gly Asn Ile Asp Thr Pro Glu Gly
245 250 255

Gly Phe Asp Ala Met Leu Gln Ala Ala Val Cys Glu Ser His Ile
260 265 270

Gly Trp Arg Lys Glu Ala Lys Arg Leu Leu Leu Val Met Thr Asp
275 280 285

Gln Thr Ser His Leu Ala Leu Asp Ser Lys Leu Ala Gly Ile Val
290 295 300

Val Pro Asn Asp Gly Asn Cys His Leu Lys Asn Asn Val Tyr Val
305 310 315

Lys Ser Thr Thr Met Glu His Pro Ser Leu Gly Gln Leu Ser Glu
320 325 330

-continued

Lys Leu Ile Asp Asn Asn Ile Asn Val Ile Phe Ala Val Gln Gly
335 340 345

Lys Gln Phe His Trp Tyr Lys Asp Leu Leu Pro Leu Leu Pro Gly
350 355 360

Thr Ile Ala Gly Glu Ile Glu Ser Lys Ala Ala Asn Leu Asn Asn
365 370 375

Leu Val Val Glu Ala Tyr Gln Lys Leu Ile Ser Glu Val Lys Val
380 385 390

Gln Val Glu Asn Gln Val Gln Gly Ile Tyr Phe Asn Ile Thr Ala
395 400 405

Ile Cys Pro Asp Gly Ser Arg Lys Pro Gly Met Glu Gly Cys Arg
410 415 420

Asn Val Thr Ser Asn Asp Glu Val Leu Phe Asn Val Thr Val Thr
425 430 435

Met Lys Lys Cys Asp Val Thr Gly Gly Lys Asn Tyr Ala Ile Ile
440 445 450

Lys Pro Ile Gly Phe Asn Glu Thr Ala Lys Ile His Ile His Arg
455 460 465

Asn Cys Ser Cys Gln Cys Glu Asp Asn Arg Gly Pro Lys Gly Lys
470 475 480

Cys Val Asp Glu Thr Phe Leu Asp Ser Lys Cys Phe Gln Cys Asp
485 490 495

Glu Asn Lys Cys His Phe Asp Glu Asp Gln Phe Ser Ser Glu Ser
500 505 510

Cys Lys Ser His Lys Asp Gln Pro Val Cys Ser Gly Arg Gly Val
515 520 525

Cys Val Cys Gly Lys Cys Ser Cys His Lys Ile Lys Leu Gly Lys
530 535 540

Val Tyr Gly Lys Tyr Cys Glu Lys Asp Asp Phe Ser Cys Pro Tyr
545 550 555

His His Gly Asn Leu Cys Ala Gly His Gly Glu Cys Glu Ala Gly
560 565 570

Arg Cys Gln Cys Phe Ser Gly Trp Glu Gly Asp Arg Cys Gln Cys
575 580 585

Pro Ser Ala Ala Ala Gln His Cys Val Asn Ser Lys Gly Gln Val
590 595 600

Cys Ser Gly Arg Gly Thr Cys Val Cys Gly Arg Cys Glu Cys Thr
605 610 615

Asp Pro Arg Ser Ile Gly Arg Phe Cys Glu His Cys Pro Thr Cys
620 625 630

Tyr Thr Ala Cys Lys Glu Asn Trp Asn Cys Met Gln Cys Leu His
635 640 645

Pro His Asn Leu Ser Gln Ala Ile Leu Asp Gln Cys Lys Thr Ser
650 655 660

Cys Ala Leu Met Glu Gln Gln His Tyr Val Asp Gln Thr Ser Glu
665 670 675

Cys Phe Ser Ser Pro Ser Tyr Leu Arg Ile Phe Phe Ile Ile Phe
680 685 690

Ile Val Thr Phe Leu Ile Gly Leu Leu Lys Val Leu Ile Ile Arg
695 700 705

Gln Val Ile Leu Gln Trp Asn Ser Asn Lys Ile Lys Ser Ser Ser
710 715 720

Asp Tyr Arg Val Ser Ala Ser Lys Lys Asp Lys Leu Ile Leu Gln
725 730 735

```
Ser Val Cys Thr Arg Ala Val Thr Tyr Arg Arg Glu Lys Pro Glu
                740                 745                 750

Glu Ile Lys Met Asp Ile Ser Lys Leu Asn Ala His Glu Thr Phe
                755                 760                 765

Arg Cys Asn Phe
            769
```

( 2 ) INFORMATION FOR SEQ ID NO:7:

( i ) SEQUENCE CHARACTERISTICS:
( A ) LENGTH: 20 amino acids
( B ) TYPE: Amino Acid
( D ) TOPOLOGY: Linear ( x i ) SEQUENCE DESCRIPTION: SEQ ID NO:7:

```
Glu Glu Ile Lys Met Asp Ile Ser Lys Leu Asn Ala His Glu Thr
  1             5                   10                  15

Phe Arg Cys Asn Phe
                20
```

( 2 ) INFORMATION FOR SEQ ID NO:8:

( i ) SEQUENCE CHARACTERISTICS:
( A ) LENGTH: 24 base pairs
( B ) TYPE: Nucleic Acid
( C ) STRANDEDNESS: Single
( D ) TOPOLOGY: Linear ( x i ) SEQUENCE DESCRIPTION: SEQ ID NO:8:

```
TTCATCATTT TCATAGTTAC ATTC 24
```

( 2 ) INFORMATION FOR SEQ ID NO:9:

( i ) SEQUENCE CHARACTERISTICS:
( A ) LENGTH: 24 base pairs
( B ) TYPE: Nucleic Acid
( C ) STRANDEDNESS: Single
( D ) TOPOLOGY: Linear ( x i ) SEQUENCE DESCRIPTION: SEQ ID NO:9:

```
CATTAAGTGT TTAAAAATCT TTTT 24
```

BETA-8 INTEGRIN SUBUNIT ANTIBODIES

CROSS-REFERENCE

This application is a divisional of copending U.S. application Ser. No. 08/193,989 filed on 9 Feb. 1994, which application is a continuation of Ser. No. 08/004,142 filed on 13 Jan. 1993, now abandoned, which application is a continuation of Ser. No. 07/670,607 filed on 14 Mar. 1991, now abandoned, which applications are incorporated herein by reference and to which applications priority is claimed under 35 USC §120.

BACKGROUND OF THE INVENTION

1. Field of the Invention

This invention relates to the isolation of a novel beta integrin subunit polypeptide and to the DNA encoding this polypeptide. The invention further relates to methods for preparing variants of this beta integrin subunit.

2. Description of Background and Related Art

The integrins are a family of plasma-membrane bound cell surface proteins. Many integrins exist; some are cell-type specific while others are present in several types of cells. At least one integrin has been found in nearly every animal cell type that has been evaluated (Hemler, *Ann. Rev. Immunol.,* 8:365 [1990]; Albelda et al., *FASEB J.,* 4:2868 [1990]) suggesting they may be ubiquitous in the animal kingdom.

Each integrin consists of an alpha polypeptide subunit and a beta polypeptide subunit. The subunits are non-covalently bound in such a way as to confer ligand-binding activity on the complex as a whole. Both types of subunits have three domains: 1) a cytoplasmic domain, which is the carboxyl terminus of the polypeptide, 2) a membrane-spanning or transmembrane domain, which is located near the carboxyl terminus and serves to anchor the polypeptide into the plasma membrane, and 3) an extracellular domain which binds ligand.

Several alpha subunits are known, (see Ruoslahti, *J. Clin. Invest.,* 87:1 [1991]), and three human beta subunits have been known for some time. Recently, three additional human beta subunits have been identified, cloned and sequenced, and named beta-4 (Suzuki et al., *EMBO J.,* 9:757 [1990]; Hogervorst et al., *EMBO J.,* 9:765 [1990]), beta-5 (McLean et al., *J. Biol. Chem.,* 265:17126 [1990]; (Ramaswarmy et al., *EMBO J.,* 9:1561 [1990]) and beta-6 (Sheppard et al., 265:11502[1990]). A seventh beta subunit, beta-7, has just been reported (Yuan et al., *Internat'l. Immunol.,* 2:1097 [1990]. Alpha and beta subunits can associate with each other in a variety of combinations thus creating a large number of distinct integrins (see Albelda et al., supra and Helmer, supra).

The human beta integrin subunits that have been identified to date share an amino acid sequence identity of around 32–56 percent and show conservation of about 50 cysteine residues (Yuan et al., supra). The beta-1 integrin subunit has an 82–90 percent homology between human, chicken, frog, and mouse (Hemler, supra), suggesting a highly conserved functional role for this subunit.

The integrins are known to mediate cell adhesion. One of the ways this mediation can occur is via the integrin binding to the extracellular matrix. Certain integrins have been shown to bind to such extracellular matrix proteins as fibronectin, fibrin, laminin, some collagens, tenascin, vitronectin, and von Willebrand factor (Ruoslahti, supra). A second way in which integrins can mediate cell adhesion is through cell-cell binding. For example, one integrin glycoprotein, IIb/IIIa, located on the surface of platelets, promotes the binding of platelets to each other via mediator molecules, especially fibrinogen. Other integrins have been shown to have a role in mediating the attachment of circulating leukocytes to tissue, thus removing them from circulation, which is important in tissue repair (Ruoslahti, supra).

It has been observed that the extracellular matrix surrounding many tumorigenic cells is less extensive than that observed for normal, non-tumorigenic cells, leading to enhanced mobility of tumor cells as compared to normal cells (Ruoslahti, supra). It has been shown that the integrin alpha-5/beta-1, as well as certain other integrins, have an altered level of expression in certain tumor cells (Plantefaber et al., *Cell,* 56:281 [1989]).

Recent research has suggested that some integrins may have a role in mediating the movement of neurons along glial fibers during development and differentiation of the cerebellum (Hatten, *Trends. Neurol Sci.,* 13:179[1990]; Sanes, *Ann. Rev. Neurosci.,* 12:491 [1989]).

There is a current and continuing need in the art to identify new integrin subunits and to identify their biological role(s), including their roles in mediating cell-cell adhesion, cell mobility, and cell adhesion to the extracellular matrix.

Accordingly, it is an object of this invention to identify a novel beta subunit integrin polypeptide that shares some common structural features with beta integrin subunits 1–7.

It is another object to provide nucleic acid encoding the novel beta integrin subunit polypeptide and to use this nucleic acid to produce the polypeptide in recombinant cell culture for research or diagnostic use, or for potential therapeutic use in certain neurological or immunological disorders and with certain tumors and tumorigenic cells.

It is a further object to provide derivatives and modified forms of the novel beta integrin subunit, including amino acid sequence variants and covalent derivatives thereof.

It is an additional object to prepare immunogens for raising antibodies against the novel beta integrin subunit, as well as to obtain antibodies capable of binding to the beta integrin subunit. It is a further object to prepare immunogens for raising antibodies against a complex comprising a novel beta integrin subunit which is associated with an alpha integrin subunit. It is preferable that the antibodies raised against these novel immunogens will not bind to beta integrin subunits 1–7.

These and other objects of the invention will be apparent to the ordinary artisan upon consideration of the specification as a whole.

SUMMARY OF THE INVENTION

These objects are accomplished, in one aspect, by providing an isolated novel beta integrin subunit polypeptide that is related structurally to beta integrin subunits 1–7. This polypeptide is hereafter termed beta-8 integrin subunit, and includes N-terminal and C-terminal fragments thereof.

In another aspect, the invention provides a composition comprising the beta-8 integrin subunit that is free of contaminating polypeptides of the animal species from which the beta-8 integrin subunit is derived In other aspects, the beta-8 integrin subunit provided is associated with an alpha integrin subunit.

The beta-8 integrin subunit or fragments thereof (which also may be synthesized by chemical methods) are fused (by recombinant expression or in vitro covalent methods) to an immunogenic polypeptide and this fusion polypeptide, in turn, is used to immunize an animal to raise antibodies against a beta-8 integrin subunit epitope. Anti-beta-8 integrin subunit antibodies are recovered from the serum of immunized animals Alternatively, monoclonal antibodies are prepared from cells of the immunized animal in conventional fashion. Antibodies identified by routine screening will bind to beta-8 integrin subunit but will not substantially cross-react with any other known beta integrin subunit, including beta integrin subunits 1–7.

Immobilized anti-beta-8 integrin subunit antibodies are useful particularly in the diagnosis (in vitro or in vivo) or purification of the beta-8 integrin subunit, e.g. a mixture of beta-8 integrin subunit is passed over a column to which the antibodies are bound.

Substitutional, deletional, or insertional variants of the beta-8 integrin subunit are prepared by in vitro or recombinant methods and screened for immuno-crossreactivity with the beta-8 integrin subunit and for beta-8 integrin subunit antagonist or agonist activity.

The beta-8 integrin subunit also is derivatized in vitro to prepare immobilized beta-8 integrin subunit and labeled beta-8 integrin subunit, particularly for purposes of diagnosis of beta-8 integrin subunit or its antibodies, or for affinity purification of beta-8 integrin subunit antibodies.

The beta-8 integrin subunit, its derivatives, or its antibodies are formulated into physiologically acceptable vehicles, especially for therapeutic use. Such vehicles include sustained-release formulations of the beta-8 integrin subunit.

In still other aspects, the invention provides an isolated nucleic acid molecule encoding the beta-8 integrin subunit, labeled or unlabeled, and a nucleic acid sequence that is complementary, or hybridizes under stringent conditions to, a nucleic acid sequence encoding the beta-8 integrin subunit, excluding nucleic acid sequences complementary to nucleic acid sequences encoding beta integrin subunits 1–7, i.e., those known beta integrin subunits that are not the beta-8 integrin subunit.

In addition, the invention provides a replicable vector comprising the nucleic acid molecule encoding the beta-8 integrin subunit operable linked to control sequences recognized by a host transformed by the vector; host cells transformed with the vector; and a method of using a nucleic acid molecule encoding the beta-8 integrin subunit to effect the production of beta-8 integrin subunit, comprising expressing the nucleic acid molecule in a culture of the transformed host cells and recovering the beta-8 integrin subunit from the host cell culture. The nucleic acid sequence is also useful in hybridization assays for beta-8 integrin subunit nucleic acid.

In further embodiments, the invention provides a method for producing beta-8 integrin subunit comprising inserting into the DNA of a cell containing the nucleic acid encoding the beta-8 integrin subunit a transcription modulatory element in sufficient proximity and orientation to the beta-8 integrin subunit nucleic acid to influence transcription thereof, with an optional further step comprising culturing the cell containing the transcription modulatory element and the beta-8 integrin subunit nucleic acid.

In still further embodiments, the invention provides a cell comprising the nucleic acid encoding the beta-8 integrin subunit and an exogenous transcription modulatory element in sufficient proximity and orientation to the beta-8 integrin subunit nucleic acid to influence transcription thereof; and a host cell containing the nucleic acid encoding the beta-8 integrin subunit operably linked to exogenous control sequences recognized by the host cell.

Still further is provided a method for obtaining cells having increased or decreased transcription of the nucleic acid encoding the beta-8 integrin subunit comprising:

(a) providing cells containing the beta-8 integrin subunit nucleic acid;

(b) introducing into the cells a transcription modulating element; and (c) screening the cells for a cell in which the transcription of the beta-8 integrin subunit nucleic acid is increased or decreased.

BRIEF DESCRIPTION OF THE DRAWINGS

FIG. 1 (SEQ. ID. NO. 3) depicts the complete nucleotide sequence of the rabbit beta-8 integrin subunit. The sequence contains an untranslated 5' region and a portion of the 3' untranslated region. The presumed ATG translation start codon is indicated. The predicted amino acid sequence is shown below the nucleotide sequence (SEQ. ID. NO. 4)

FIG. 2 (SEQ. ID. NO. 3) depicts the complete nucleotide sequence of the beta-8 integrin subunit from the human osteosarcoma cell line MG-63 described in the examples The sequence contains an untranslated 5' region and a 3' untranslated region. The presumed ATG translation start codon is indicated,. The predicted amino acid sequence is shown below the nucleotide sequence (SEQ. ID. No. 5).

DETAILED DESCRIPTION OF THE PREFERRED EMBODIMENTS

I. Definitions

In general, the following words or phrases have the indicated definition when used in the description, examples, and claims:

The term "beta-8 integrin subunit" or "β-8 integrin subunit" is defined as a polypeptide having a qualitative biological activity in common with the beta-8 integrin subunit of FIG. 1 or FIG. 2, and which has at least 75% amino acid sequence identity with the beta-8 integrin subunit of FIG. 1 or FIG. 2. Preferably the beta-8 integrin subunit comprises at least 5 amino acid residues Identity or homology with respect to a beta-8 integrin subunit in defined herein as the percentage of amino acid residues in the candidate sequence that are identical with the residues in FIG. 1 or FIG. 2, after aligning the sequences and introducing gaps, if necessary, to achieve the maximum percent homology, and not considering any conservative substitutions as part of the sequence identity. Neither N- nor C-terminal extensions nor insertions shall be construed as reducing identity or homology.

Beta-8 integrin subunit qualitative biological activity is defined as either 1) immunological cross-reactivity with at least one epitope of the beta-8 integrin subunit, or 2) the possession of at least one adhesive, regulatory or effector function qualitatively in common with the beta-8 integrin subunit.

Immunologically cross-reactive as used herein means that the candidate polypeptide is capable of competitively inhibiting the qualitative biological activity of the beta-8 integrin subunit having this activity with polyclonal antibodies or antisera raised against the known active analogue. Such antibodies and antisera are prepared in conventional fashion by injecting an animal such as a goat or rabbit, for example, subcutaneously with the known native beta-8 integrin subunit in complete Freund's adjuvant, followed by booster intraperitoneal or subcutaneous injection in incomplete Freund's.

Included within the scope of the beta-8 integrin subunit as that term is used herein are beta-8 integrin subunits having the translated or translated mature amino acid sequences of the rabbit or human beta-8 integrin subunits as set forth in FIG. 1 or FIG. 2, deglycosylated or unglycosylated derivative of the beta-8 integrin subunit, homologous amino acid sequence variants of the sequence of FIG. 1 or FIG. 2, and homologous in vitro-generated variants and derivatives of the beta-8 integrin subunit, which are capable of exhibiting a biological activity in common with the beta-8 integrin subunit of FIG. 1 or FIG. 2. While native beta-8 integrin subunit is a membrane-bound polypeptide, soluble forms, such as those form lacking a functional transmembrane domain, are also included within this definition.

Also included within the scope of this invention is a polypeptide or protein encoded by the human beta-8 integrin subunit nucleotide sequence set forth in FIG. 2; fragments thereof having 15 and preferably 30 amino acid residues; fragments thereof having greater than about 5 residues comprising an immune epitope or other biologically active site of the beta-8 integrin subunit; amino acid sequence variants of said FIG. 1 or FIG. 2 sequence wherein an amino acid residue has been inserted N- or C-terminal to, or within, said FIG. 1 or FIG. 2 sequence or its fragment as defined above; and/or amino acid sequence variants of said FIG. 1 or FIG. 2 sequence or its fragment as defined above wherein an amino acid residue of said FIG. 1 or FIG. 2 sequence or fragment thereof has been substituted by another residue, including predetermined mutations by, e.g., site-directed or PCR mutagenesis, and other animal species of the beta-8 integrin subunit such as rabbit, rat, porcine, non-human primate, equine, murine, and ovine beta-8 integrin subunit and alleles and other naturally occurring variants of the foregoing and human sequences; and derivatives of the beta-8 integrin subunit or its fragments as defined above wherein the beta-8 integrin subunit or its fragments have been covalently modified by substitution, chemical, enzymatic, or other appropriate means, with a moiety other than a naturally occurring amino acid. Such fragments and variants exclude any polypeptide heretofore identified, including any known beta integrin subunits of any animal species or any known fragment of such beta integrin subunits including beta integrin subunits 1–7. Beta-8 integrin subunit amino acid sequence variants generally will share at least about 75% (preferably >80%, more preferably >85%) sequence identity with the translated sequence shown in FIG. 1 or FIG. 2.

The preferred beta-8 integrin subunit is human beta-8 integrin subunit. The human beta-8 integrin shares a polypeptide sequence identity of about 35%, 32%, 34%, 31%, 34%, 37% and 31% with known human beta integrins subunits 1–7, respectively.

"Isolated" beta-8 integrin subunit nucleic acid or polypeptide is beta-8 integrin subunit nucleic acid or polypeptide that is identified and separated from contaminant nucleic acids or polypeptides present in the animal or human source of the beta-8 integrin nucleic acid or polypeptide. The nucleic acid or polypeptide may be labeled for diagnostic and probe purposes, using a label as described and defined further below in the discussion of diagnostic assays. The isolated beta-8 integrin subunit may be associated with any alpha integrin subunit to form a complex, as for example in an alpha-v/beta-8 complex. Associated complexes comprising truncated forms of the beta-8 integrin subunit and/or the alpha integrin subunit are also contemplated by this invention.

Beta-8 integrin subunit "nucleic acid" is defined as RNA or DNA containing greater than ten (10) bases that encodes a beta-8 integrin subunit, is complementary to nucleic acid sequence encoding the beta-8 integrin subunit, hybridizes to such nucleic acid and remains stably bound to it under stringent conditions, or encodes a polypeptide sharing at least 75% sequence identity, preferably at least 80%, and more preferably at least 85%, with the translated amino acid sequence shown in FIG. 4. Preferably the DNA which hybridizes to the nucleic acid of FIG. 1 or FIG. 2 contains at least 20, more preferably 40, and even more preferably 60 bases. Most preferably, the hybridizing DNA or RNA contains 45 or even more preferably 90 bases. Such hybridizing or complementary nucleic acid, however, is defined further as being novel and unobvious over any prior art nucleic acid including that which encodes, hybridizes under stringent conditions, or is complementary to nucleic acid encoding a known beta integrin subunit, including beta integrin subunits 1–7.

"Stringent conditions" are those that (1) employ low ionic strength and high temperature for washing, for example, 0015M NaCl/00015M sodium citrate10.1% $NaDodSO_4$ at 50° C., or (2) employ during hybridization a denaturing agent such as formamide, for example, 50% (vol/vol) formamide with 0.1% bovine serum albumin10.1% Ficoll10.1% polyvinylpyrrolidone/50 mM sodium phosphate buffer at pH 65 with 750 mM NaCl, 75 mM sodium citrate at 42° C. Another example is use of 50% formamide, 5×SSC (0.75M NaCl, 0.075M sodium citrate), 50 mM sodium phosphate (pH 68), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures In addition, other equivalent plasmids are known in the art and will be apparent to the ordinary artisan.

"Restriction Enzyme Digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1–2 units of enzyme in about 20 μl of buffer solution. Appropriate buffers and substrate amounts for particular restriction enzymes are specified by the manufacturer, Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., (*Molecular Cloning: A Laboratory Manual* New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the get section containing the desired fragment, and separation of the gel from DNA. This procedure is known generally. For example, see Lawn et al., *Nucleic Acids Res.,* 9: 6103–6114 (1981), and Goeddel et al., *Nculeic Acids Res.* 8:4057 (1980).

"Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane supports for analysis with a radiolabeled, biotinylated or enzyme-labeled probe as described in sections 9.37–9.52 of Sambrook et al., supra.

"Northern analysis" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 μg of DNA If the DNA is to be ligated into a vector. The vector is first linearized by digestion with the appropriate restriction endonuclease(s). The linearized fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single-or double-stranded polydeoxynucleotides that are chemically synthesized by known methods (such as phosphotriester, phosphite, or phosphoramidite chemistry, using solid phase techniques such as described in EP 266,032 published 4 May 1988, or via deoxynucleoside H-phosphonate intermediates as described by Froehler et al., *Nucl. Acids Res.,* 14:5399–5407 [1986]). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., *PCR Technology,* (Stockton Press, NY, 1989). As used herein, PCR is considered to be one, but not the only, example of a nucleic acid polymerase reaction method for amplifying a nucleic acid test sample, comprising the use of a known nucleic acid as a primer and utilizes a nucleic acid polymerase to amplify or generate a specific piece of nucleic acid.

II. Suitable Methods for Practicing the Invention

1. Preparation of Native Beta-8 Integrin Subunit and Variants

A. Isolation of DNA Encoding Beta-8 Integrin Subunit

The DNA encoding the beta-8 integrin subunit may be obtained from any cDNA library prepared from tissue believed to possess the beta-8 integrin subunit mRNA and to express it at a detectable level. The beta-8 integrin subunit gene may also be obtained from a genomic library. Libraries are screened with probes designed to identify the gene of interest or the protein encoded by it. For cDNA expression libraries, suitable probes include monoclonal or polyclonal antibodies that recognize and specifically bind to the beta-8 integrin subunit; oligonucleotides of about 20–80 bases in length that encode known or suspected portions of the beta-8 integrin subunit cDNA from the same or different species; and/or complementary or homologous cDNAs or fragments thereof that encode the same or a similar gene. Appropriate probes for screening genomic DNA libraries include, but are not limited to, oligonucleotides; cDNAs or fragments thereof that encode the same or a similar gene; and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding beta-8 integrin is to use polymerase chain reaction (PCR) methodology as described in section 14 of Sambrook et al., supra. This method requires the use of oligonucleotide probes that will hybridize to the beta-8 integrin. Strategies for selection of oligonucleotides are described below.

Another alternative method for obtaining the gone of interest is to chemically synthesize it using one of the methods described in Engels et al., (*Agnew. Chem. Int. Ed. Engl.*, 28:716–734 [1989]), specifically incorporated by reference. These methods include triester, phosphite, phosphoramidite and H-Phosphonate methods, PCR and other autoprimer methods, and oligonucleotide syntheses on solid supports. These methods may be used if the entire nucleic acid sequence of the gone is known, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various tissues, preferably mammalian placental, fetal, brain, and carcinoma cell lines. More preferably, human or rabbit placental, fetal, brain, and carcinoma cell line cDNA libraries are screened with the oligonucleotide probes.

The oligonucleotide sequences selected as probes should be of sufficient length and sufficiently unambiguous that false positives are minimized. The actual nucleotide sequence(s) is usually based on conserved or highly homologous nucleotide sequences or regions of other beta integrin subunits. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use 32-P labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the beta-8 integrin subunit nucleic acid that encodes a fulllength polypeptide. In some preferred embodiments, the nucleic acid sequence includes the native beta-8 integrin subunit signal sequence. Nucleic acid having all the protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of the Beta-8 Integrin Subunit

Amino acid sequence variants of the beta-8 integrin subunit are prepared by introducing appropriate nucleotide changes into the beta-8 integrin subunit DNA, or by in vitro synthesis of the desired beta-8 integrin polypeptide. Such variants include, for example, deletions from, or insertions or substitutions of, residues within the amino acid sequence shown for the human beta-8 integrin subunit in FIG. 2. Any combination of deletion, insertion, and substitution can be made to arrive at the final construct, provided that the final construct possesses the desired characteristics. Excluded from the scope of this invention are beta-8 variants or polypeptide sequences that are not novel and unobvious over the prior art. The amino acid changes also may alter post-translational processes of the beta-8 integrin subunit, such as changing the number or position of glycosylation sites, altering the membrane anchoring characteristics, and/or altering the intra-cellular location of the beta-8 integrin subunit by inserting, deleting, or otherwise affecting the leader sequence of the native beta-8 integrin subunit.

In designing amino acid sequence variants of beta-8 integrin subunits, the location of the mutation site and the nature of the mutation will depend on the beta-8 integrin subunit characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the beta-8 integrin subunit polypeptide that are preferred locations for mutagenesis is called "alanine scanning mutagenesis" as described by Cunningham and Wells (Science, 244:1081–1085 [1989]). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed beta-8 integrin subunit variants are screened for the optimal combination of desired activity.

In general, the regions of the beta-8 integrin subunit molecule preferred for alterations are the regions that are highly conserved with respect to other known beta integrin subunits. For example, the region between amino acids 118 and 180 of the human beta-8 integrin (numbered according to FIG. 2) is highly homologous with other beta integrins, and thus is a preferred region for mutations. Another preferred region is the region between amino acids 240 and 275. Amino acid sequence deletions generally range from about 1 to 30 residues, more preferably about 1 to 10 residues, and typically are contiguous Deletions may be introduced into regions of low homology between the beta-8 integrin subunit and other beta integrin subunits to modify the activity of the beta-8 integrin subunit Deletions from the beta-8 integrin subunit in areas of substantial hornology with any other beta integrin subunits will be more likely to modify the biological activity of the beta-8 integrin subunit more significantly. The number of consecutive deletions will be selected so as to preserve the tertiary structure of beta-8 integrin in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues Intrasequence insertions (i.e., insertions within the beta-8 integrin sequence) may range generally from about 1 to 10 residues, more preferably 1 to 5, most preferably 1 to 3. Examples of terminal insertions include the beta-8 integrin subunit with an N-terminal methionyl residue, an artifact of the direct expression of beta-8 integrin in bacterial recombinant cell culture, and fusion of a heterotogous N-terminal signal sequence to the N-terminus of the beta-8 integrin subunit molecule to facilitate the secretion of the mature beta-8 integrin subunit from recombinant host cells. Such signal sequences generally will be obtained from, and thus homologous to, the intended host cell species. Suitable sequences include STII or Ipp for *E. coli.*, alpha factor for yeast, and viral signals such as herpes gD for mammalian cells.

Other insertional variants of the beta-8 integrin subunit include the fusion to the N- or C-terminus of the beta-8 integrin subunit of immunogenic polypeptides, e.g., bacterial polypeptides such as beta-lactamase or an enzyme encoded by the *E. coli.* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

Another group of variants are amino acid substitution variants. These variants have at least one amino acid residue in the beta-8 integrin subunit molecule removed and a different residue inserted in its place. The sites of greatest interest for substitutional mutagenesis include sites identified as the active site(s) of the beta-8 integrin subunit, and sites where the amino acids found in the beta-8 integrin subunit from various species are substantially different in terms of side-chain bulk, charge, and/or hydrophobicity.

Other sites of interest are those in which particular residues of the beta-8 integrins obtained from various species are identical. These positions may the important for the biological activity of the beta-8 integrin subunit. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the beta-8 integrin subunit are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, lie;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another. Such substituted residues may be introduced into regions of the beta-8 integrin subunit that are homologous with other integrins, or, more preferably, into the nonhomologous regions of the molecule.

In one embodiment of the invention, it is desirable to inactivate one or more protease cleavage sites that are present in the molecule. These sites are identified by inspection of the encoded amino acid sequence. Where protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of beta-8 integrin also may be substituted, generally with serine, to improve the oxidative stability of the molecule and prevent aberrant crosslinking.

DNA encoding amino acid sequence variants of the beta-8 integrin subunit is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the beta-8 integrin subunit.

Oligonucleotide-mediated mutagenesis is a preferred method for preparing substitution, deletion, and insertion variants of beta-8 integrin DNA. This technique is well known in the art as described by Adelman et al., DNA, 2:183 (1983) Briefly, the beta-8 integrin subunit DNA is altered by hybridizing an oligonucleotide encoding the desired mutation to a DNA template, where the template is the single-stranded form of a plasmid or bacteriophage containing the unaltered or native DNA sequence of the beta-8 integrin subunit. After hybridization, a DNA polymerase is used to synthesize an entire second complementary strand of the template that will thus incorporate the oligonucleotide primer, and will code for the selected alteration in the beta-8 integrin subunit DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., (*Proc. Natl. Acad. Sci. USA,* 75:5765 [1978]).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the beta-8 integrin subunit, and the other strand (the original template) encodes the native, unaltered sequence of the beta-8 integrin subunit. This heteroduplex molecule is then transformed into a suitable host cell, usually a prokaryote such as *E. coli.* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding beta-8 integrin subunit mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of beta-8 integrin. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA.

It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid. DNA outside of the region to be amplified. Of this material, 100 ng is added to a PCR mixture containing PCR buffer, which contains the four deoxynucleotide triphosphates and is included in the GENEAMP® kits (obtained from Perkin-Elmer Cetus, Norwalk, CT and Emeryville, CA), and 25 pmole of each oligonucleotide primer, to a final volume of 50 μl. The reaction mixture is overlayed with 35 μl mineral oil. The reaction is denatured for 5 minutes at 100° C., placed briefly on ice, and then 1 μl Thermus aquaticus (Taq) DNA polymerase (5 units/μl, purchased from Perkin-Elmer Cetus, Norwalk, CT and Emeryville, CA) is added below the mineral oil layer. The reaction mixture is then inserted into a DNA. Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., (*Gene,* 34:315 [1985]). The starting material is the plasmid (or other vector) comprising the beta-8 integrin subunit DNA to be mutated. The codon(s) in the beta-8 integrin subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the beta-8 integrin subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated beta-8 integrin subunit DNA sequence.

C Insertion of DNA into a Cloning Vehicle

The cDNA or genomic DNA encoding native or variant beta-8 integrin subunit is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the beta-8 integrin subunit DNA that is inserted into the vector. The native pro beta-8 integrin subunit DNA encodes a signal sequence at the amino terminus (5' end of the DNA) of the polypeptide that is cleaved during post-translational processing of the polypeptide to form the mature beta-8 integrin subunit polypeptide Native beta-8 integrin subunit is not however secreted from the cell as it contains a membrane anchoring domain near the carboxyl terminus of the polypeptide. Thus, to form a secreted version of beta-8 integrin subunit, the carboxyl terminal domain of the molecule, including the membrane anchoring domain, is ordinarily deleted. This truncated variant beta-8 integrin subunit polypeptide may be secreted from the cell, provided that the DNA encoding the truncated variant retains the amino terminal signal sequence.

Included within the scope of this invention are beta-8 integrin subunits with the native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native beta-8 integrin subunit signal sequence, the signal sequence is substituted by a prokaryotic signal sequence selected, for example, from the group of the alkaline phosphatase, penicillinase, Ipp, or heat-stable enterotoxin II leaders. For yeast secretion the native beta-8 integrin subunit signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the beta-8 integrin subunit DNA. However, the recovery of genomic DNA encoding the beta-8 integrin subunit is more complex than that of an exogenously replicated vector because restriction enzyme digestion is required to excise the beta-8 integrin subunit DNA.

(iii) Selection Gene Component

Expression and cloning vectors should contain a selection gene, also termed a selectable marker. This gene encodes a protein necessary for the survival or growth of transformed host cells grown in a selective culture medium Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding Dalanine racemase for Bacilli.

One example of a selection scheme utilizes a drug to arrest growth of a host cell. Those cells that are successfully transformed with a heterologous gene express a protein conferring drug resistance and thus survive the selection regimen Examples of such dominant selection use the drugs neomycin (Southern et al., *J. Molec. Appl. Genet.*, 1:327 [1982]), mycophenolic acid (Mulligan et al., *Science*, 209:1422 [1980]) or hygromycin (Sugden et al., *Mol. Cell. Biol.*, 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the beta-8 integrin subunit nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the beta-8 integrin subunit. Amplification is the process by which genes in greater demand for the production of a protein critical for growth are reiterated in tandem within the chromosomes of successive generations of recombinant cells. Increased quantities of the beta-8 integrin subunit are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77:4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding the beta-8 integrin subunit. This amplification technique can be used with any otherwise suitable host, e.g., ATCC No CCL61 CHO-K1, notwithstanding the presence of endogenous DHFR if, for example, a mutant DHFR gene that is highly resistant to Mtx is employed (EEP 117,060). Alternatively, host cells (particularly wild-type hosts that contain endogenous DHFR) transformed or co-transformed with DNA sequences encoding the beta-8 integrin subunit, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418 See U.S. Pat. No. 4,965,199.

A suitable selection gene for use in yeast is the trp1 gene present in the yeast plasmid Yrp7 (Stinchcomb et al., *Nature*, 282:39 [1979]; Kingsman et al., *Gene*, 7:141 [1979]; or Tschemper et al., *Gene*, 10:157 [1980]). The trp1 gene provides a selection marker for a mutant strain of yeast lacking the ability to grow in tryptophan, for example, ATCC No. 44076 or PEP4–1 (Jones, Genetics, 85:12 [1977] ). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the beta-8 integrin subunit nucleic acid. Promoters are untranslated sequences located upstream (5') to the start codon of a structural gene (generally within about 100 to 1000 bp) that control the transcription and translation of a particular nucleic acid sequence, such as the beta-8 integrin subunit, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the beta-8 integrin subunit by removing the promoter from the source DNA by restriction enzyme digestion and inserting the isolated promoter sequence into the vector. Both the native beta-8 integrin subunit promoter sequence and many heterologous promoters may be used to direct amplification and/or expression of the beta-8 integrin subunit DNA. However, heterologous promoters are preferred, as they generally permit greater transcription and higher yields of expressed beta-8 integrin subunit as compared to the native beta-8 integrin subunit promoter.

Promoters suitable for use with prokaryotic hosts include the β-lactamase and lactose promoter systems (Chang et al., *Nature*, 275:615 [1978]; and Goeddel et al., Nature, 281: 544 [1979]), alkaline phosphatase, a tryptophan (trp) promoter system (Goeddel, *Nucleic Acids Res*, 8:4057 [1980]

and EP 36,776) and hybrid promoters such as the tac promoter (deBoer et al., *Proc. Natl. Acad. Sci. USA,* 80:21–25 [1983]). However, other known bacterial promoters are suitable. Their nucleotide sequences have been published, thereby enabling a skilled worker operably to ligate them to DNA encoding the beta-8 integrin subunit (Siebenlist et al., Cell, 20:269 [1980]) using linkers or adaptors to supply any required restriction sites. Promoters for use in bacterial systems also generally will contain a Shine-Dalgarno (SD) sequence operably linked to the DNA encoding the beta-8 integrin subunit.

Suitable promoting sequences for use with yeast hosts include the promoters for 3phosphoglycerate kinase (Hitzeman et al., *J. Biol. Chem.,* 255:2073 [1980]) or other glycolytic enzymes (Hess et al., *J. Adv. Enzyme Reg.,* 7:149 [1968]; and Holland, Biochemistry, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657. A Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly. A tail to the 3' end of the coding sequence. All of these sequences are suitably inserted into mammalian expression vectors.

Beta-8 integrin subunit transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the beta-8 integrin subunit sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan and Berg, *Science,* 209:1422–1427 (1980); Pavlakis et al., *Proc Natl. Acad. Sci. USA,* 78:7398–7402 (1981). The immediate early promoter of the human cytomegalovirus is conveniently obtained as a HindIII E restriction fragment Greenaway et al., *Gene,* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503–508 (1982) on expressing cDNA encoding immune interferon in monkey cells; Reyes et al., *Nature,* 297: 598–601 (1982) on expression of human β-interferon cDNA in mouse cells under the control of a thymidine kinase promoter from herpes simplex virus, Canaani and Berg, *Proc. Natl. Acad. Sci. USA,* 79:5166–5170 (1982) on expression of the human interferon β1 gene in cultured mouse and rabbit cells, and Gorman et al., *Proc. Natl. Acad. Sci. USA,* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the beta-8 integrin subunit of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA,* 78:993 [1981]) and 3' (Lusky et al., *Mol. Cell. Bio.,* 3:1108 [1983]) to the transcription unit, within an intron (Baneall et al., *Cell,* 33:729 [1983]) as well as within the coding sequence itself (Osborne et al., *Mol. Cell Bio.,* 4:1293 [1984]). Many enhancer sequences are now know from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297:17–18 (1982) on enhancing elements for activation of eukaryotic promoters. The enhancer may be spliced into the vector at a position 5' or 3' to the beta-8 integrin subunit DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the beta-8 integrin subunit. The 3' untranslated regions also include transcription termination sites.

Construction of suitable vectors containing one or more of the above listed components the desired coding and control sequences employs standard ligation techniques Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate Plasmids from the transformants are prepared, analyzed by restriction endonuclease digestion, and/or sequenced by the method of Messing et al., *Nucleic Acids Res,* 9:309 (1981) or by the method of Maxam et al., *Methods in Enzymology,* 65:499 (1980).

Particularly useful in the practice of this invention are expression vectors that provide for the transient expression in mammalian cells of DNA encoding the beta-8 integrin subunit. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the beta-8 integrin subunit that have beta-8 integrin subunit-like activity.

Other methods, vectors, and host cells suitable for adaptation to the synthesis of the beta-8 integrin subunit in recombinant vertebrate cell culture are described in Gething et al., *Nature,* 293:620–625 [1981]; Mantel et al., *Nature,* 281: 40–46 [1979]; Levinson et al.,; EP 117,060; and EP 117,058. A particularly useful plasmid for mammalian cell culture expression of the beta-8 integrin subunit is pRK5 (EP pub no 307,247) or pSVI6B (U.S. Ser. No. 07/441,574 filed 22 Nov. 1989, the disclosure of which is incorporated herein by reference).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli,* Bacilli such as B. subtilis, Pseudomonas species such as *P. aeruginosa, Salmonella typhimuriun,* or *Serratia marcescans.* One preferred *E. coli* clining host is *E. coli* 294 (ATCC 31,446), although other strains such as *E. coli* B, *E. coli* $_{X}$1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for vectors containing beta-8 integrin subunit DNA. *Saccharomyces cerevisiae,* or common baker's yeast, is the most commonly used among lower eukaryotic host microorganisms. However, a number of other genera, species, and strains are commonly available and useful herein, such as *S. pombe* [Beach and Nurse, *Nature,* 290:140 [1981)], *Kluyveromycer lactis* [Louvencourt et al., *J. Bacteriol.,* 737 (1983)], yarrowla [EP 402,226], *Pichia pastorias* [EP 183,070], *Trichoderma reesia* [EP 244,234], *Neuorspora crassa* [Case et al., *Proc. Natl. Acad. Sci. USA,* 76:5259–5263 (1979)], and Aspergillus hosts such as *A. nidulans* [Ballance et al., *Biochem. Biophys. Res. Commun.,* 112:284–289 (1983); Tilburn et al., *Gene,* 26:205–221 (1983); Yelton et al., *Proc. Natl. Acad. Sci. USA,* 81:1470–1474 (1984)] and *A. niger* [Kelly and Hynes, *EMBO J.,* 4:475–479 (1985)].

Suitable host cells for the expression of glycosylated beta-8 integrin subunit polypeptide are derived from multicellular organisms. Such host cells are capable of complex processing and glycosylation activities. In principle, any higher eukaryotic cell culture is workable, whether from vertebrate or invertebrate culture Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictur albopictus* (mosquito), *Drosophila melanogaster* (fruitfly), and *Bombyx mori* host cells have been identified See, e.g., Luckow et al., Bio/Technology, 6:47–55 (1988); Miller et al., in *Genetic Engineering,* Setlow, J. K. et al., eds., Vol. 8 (Plenum Publishing, 1986), pp. 277–279; and Maeda et al., *Nature,* 315:592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the beta-8 integrin DNA. During incubation of the plant cell culture with *A. tumefaciens,* the DNA encoding beta-8 integrin is transferred to the plant cell host such that it is transfected, and will, under appropriate conditions, express the beta-8 integrin DNA. In addition, regulatory and signal sequences compatible with plant cells are available, such as the nopaline synthase promoter and polyadenylation signal sequences. Depicker et al., *J. Mol. Appl. Gen.,* 1:561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989 .

However, interest has been greatest in vertebrate cells, and propagation of vertebrate cells in culture (tissue culture) has become a routine procedure in recent years [*Tissue Culture,* Academic Press, Kruse and Patterson, editors (1973)]. Examples of useful mammalian host cell lines are monkey kidney CV1 line transformed by SV40 (COS-7, ATCC CRL 1651 ); human embryonic kidney line (293 or 293 cells subcloned for growth in suspension culture, Graham et al., *J. Gen Virol.,* 36:59 [1977]); baby hamster kidney cells (BHK, ATCC CCL 10); Chinese hamster ovary cells/-DHFR (CHO, Urlaub and Chasin, *Proc. Natl. Acad. Sci. USA,* 77:4216 [1980]); mouse sertoli cells (TM4, Mather, *Biol. Reprod.,* 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse-mammary tumor (MMT 060562, ATCC CCL51 ); TRI cells (Mather et al., *Annals N.Y. Acad. Sci.,* 383:44–68 [1982]); MRC 5 cells; FS4 cells; and a human hepatoma cell line (Hep G2) Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells such as by nuclear injection, electroporation, or by protoplast fusion may also be used.

E. Culturing the Host Cells

Prokaryotic cells used to produce the beta-8 integrin subunit polypeptide of this invention are cultured in suitable media as described generally in Sambrook et al., supra.

The mammalian host cells used to produce the beta-8 integrin subunit of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58:44(1979), Barnes and Sato, *Anal. Biochem.*, 102:255 (1980), U.S. Pat. No. 4,767,704; 4,657,866; 4,927,762; or 4,560,655; WO 90/03430; WO 87/00195; U.S. Pat. Re. 30,985; or copending U.S. Ser. No. 07/592,107 or 071592,141, both filed in 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the beta-8 integrin subunit of this invention may be produced by homologous recombination, or with recombinant production methods utilizing control elements introduced into cells already containing DNA encoding the beta-8 integrin subunit currently in use in the field. For example, a powerful promoter/enhancer element, a suppressor, or an exogenous transcription modulatory element is inserted in the genome of the intended host cell in proximity and orientation sufficient to influence the transcription of DNA encoding the desired beta-8 integrin subunit. The control element does not encode the beta-8 integrin subunit of this invention, but the DNA is present in the host cell genome. One next screens for cells making the beta-8 integrin subunit of this invention, or increased or decreased levels of expression, as desired.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77:5201–5205 [1980]), dot blotting (DNA analysis), or in situ hybridization, using an appropriately labeled probe, based on the sequences provided herein Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

Antibodies useful for immunohistochemical staining and/or assay of sample fluids may be either monoclonal or polyclonal, and may be prepared in any mammal. Conveniently, the antibodies may be prepared against a native beta-8 integrin subunit polypeptide or against a synthetic peptide based on the DNA sequences provided herein as described further in Section 4 below.

G. Purification of The Beta-8 Integrin Subunit Polypeptide

The beta-8 integrin subunit preferably is recovered from the culture medium as a secreted polypeptide, although it also may be recovered from host cell lysates when directly expressed without a secretory signal.

When the beta-8 integrin subunit is produced in cultured cells which normally produce alpha integrin subunits (such as 293 cells), frequently the alpha and beta subunits will be found associated in a complex. This complex may be found in the membrane or in the cytoplasm of the cell, or in the cell culture medium if it is a truncated beta-8 integrin subunit which is expressed with a functional signal sequence. The alpha and beta subunits may be separated from each other for purposes of purification by treating the complex with EDTA, EGTA, or other calcium and cation chelator. When the alpha/beta-8 integrin complex is disrupted, some changes in tertiary conformation of either subunit may result, and these changes may affect the biological activity of either subunit. It may be possible to avoid formation of the complex by selecting host cells which do not produce an alpha subunit, or by transfecting host cells with beta-8 integrin fragments.

When the beta-8 integrin subunit is expressed in a recombinant cell other than one of human origin, the beta-8 integrin subunit is completely free of proteins or polypeptides of human origin. However, it is necessary to purify the beta-8 integrin subunit from recombinant cell proteins or polypeptides to obtain preparations that are substantially homogeneous as to the beta-8 integrin subunit. As a first step, the culture medium or lysate is centrifuged to remove particulate cell debris. The membrane and soluble protein fractions are then separated. The beta-8 integrin subunit may then be purified from the soluble protein fraction and from the membrane fraction of the culture lysate, depending on whether the beta-8 integrin subunit is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGEE; ammonium sulfate precipitation; gel filtration using, for example, Sephadex G-75; and protein A Sepharose columns to remove contaminants such as IgG.

Beta-8 integrin subunit variants in which residues have been deleted, inserted or substituted are recovered in the same fashion as the native beta-8 integrin subunit, taking account of any substantial changes in properties occasioned by the variation. For example, preparation of a beta-8 integrin subunit fusion with another protein or polypeptide, e.g. a bacterial or viral antigen, facilitates purification; an immunoaffinity column containing antibody to the antigen can be used to adsorb the fusion. Immunoaffinity columns such as a rabbit polyclonal anti-beta-8 integrin subunit column can be employed to absorb the beta-8 integrin subunit variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native beta-8 integrin subunit may require modification to account for changes in the character of the beta-8 integrin subunit or its variants upon expression in recombinant cell culture.

H. Covalent Modifications of Beta-8 Integrin Subunit Polypeptides

Covalent modifications of beta-8 integrin subunit polypeptides are included within the scope of this invention Both native beta-8 integrin subunits and amino acid sequence variants of the beta-8 integrin subunit may be covalently modified. One type of covalent modification included within the scope of this invention is a beta-8 integrin subunit polypeptide fragment Beta-8 integrin subunit fragments having up to about 40 amino acid residues may be conveniently prepared by chemical synthesis, or by enzymatic or chemical cleavage of the full-length beta-8 integrin subunit polypeptide or beta-8 integrin subunit variant polypeptide. Other types of covalent modifications of the beta-8 integrin subunit or fragments thereof are introduced into the molecule by reacting targeted amino acid residues of the beta-8 integrin subunit or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{135}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking beta-8 integrin to a water-insoluble support matrix or surface for use in the method for purifying anti-beta-8 integrin subunit antibodies, and vice versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co, San Francisco, p.p. 79–86 [1983]), acetylation of the N-terminal amine, and amidation of any C-terminal carboxyl group.

Another type of covalent modification of the beta-8 polypeptide included within the scope of this invention comprises altering the native glycosylation pattern of the polypeptide. By altering is meant deleting one or more carbohydrate moieties found in native beta-8, and/or adding one or more glycosylation sites that are not present in the native beta-8 polypeptide.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the beta-8 integrin polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native beta-8 integrin subunit sequence (for 0-linked glycosylation sites). For ease, the beta-8 integrin subunit amino acid sequence is preferably altered through changes at the DNA level, particularly by mutating the DNA encoding the beta-8 integrin subunit polypeptide at preselected bases such that codons are generated that will translate into the desired amino acids. The DNA mutation(s) may be made using methods described above under the heading of "Amino Acid Sequence Variants of Beta-8 Integrin Subunit Polypeptide".

Another means of increasing the number of carbohydrate moieties on the beta-8 polypeptide is by chemical or enzymatic coupling of glycosides to the polypeptide. These procedures are advantageous in that they do not require production of the polypeptide in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston (*CRC Crit. Rev. Biochem.,* pp. 259–306 [1981]).

Removal of carbohydrate moieties present on the native beta-8 integrin subunit polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al. (*Arch. Biochem. Biophys.,* 259:52 [1987]) and by Edge et al., (*Anal. Biochem.,* 118:131 [1981 ]). Enzymatic cleavage of carbohydrate moieties on polypeptides can be achieved by the use of a variety of endo- and exo- glycosidases as described by. Thotakura et al., (*Meth. Enzymol.,* 138:350 [1987]).

Glycosylation at potential glycosylation sites may be prevented by the use of the compound tunicamycin as described by Duskin et al., (*J. Biol. Chem.,* 257:3105 [1982]). Tunicamycin blocks the formation of protein-N-glycoside linkages.

Another type of covalent modification of the beta-8 integrin subunit comprises linking the beta-8 integrin subunit polypeptide to various nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The beta-8 integrin subunit also may be entrapped in microcapsules prepared, for example, by coacervation techniques or by interfacial polymerization (for example, hydroxymethylcellulose orgelatin-microcapsulesand poly-[methylmethacylate]microcapsules, respectively), in colloidal drug delivery systems (for example, liposomes, albumin microspheres, microemulsions, nano-particles and nanocapsules), or in microemulsions. Such techniques are disclosed in *Remington's Pharmaceutical Sciences,* 16th edition, Osol, A., Ed., (1980).

Beta-8 integrin subunit preparations are also useful in generating antibodies, as standards in assays for the beta-8 integrin subunit (e.g. by labeling the beta-8 integrin subunit for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant beta-8 integrin subunit, it will be appreciated that some screening of the recovered variant will be needed to select the optimal variant. For example, a change in the immunological character of the beta-8 integrin subunit molecule, such as affinity for a given antibody, is measured by a competitive-type immunoassay. The variant is assayed for changes in the suppression or enhancement of its activity by comparison to the activity observed for native beta-8 integrin subunit in the same assay Other potential modifications of protein or polypeptide properties such as redox or thermal stability, hydrophobicity, susceptibility to proteolytic degradation, or the tendency to aggregate with carriers or into multimars are assayed by methods well known in the art.

3. Therapeutic Compositions and Administration of Beta-8 Integrin

Therapeutic formulations of beta-8 integrin subunit are prepared for storage by mixing beta-8 integrin subunit having the desired degree of purity with optional physiologically acceptable carriers, excipients, or stabilizers (*Remington's Pharmaceutical Sciences,* supra), in the form of lyophilized cake or aqueous solutions Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; saltforming counterions such as sodium; and/or nonionic surfactants such as Tween, Pluronics or polyethylene glycol (PEG).

The beta-8 integrin subunit to be used for in vivo administration must be sterile. This is readily accomplished by filtration through sterile filtration membranes, prior to or following lyophilization and reconstitution. The beta-8 integrin subunit ordinarily will be stored in lyophilized form or in solution.

Therapeutic beta-8 integrin subunit compositions generally are placed into a container having a sterile access port, for example, an intravenous solution bag or vial having a stopper pierceable by a hypodermic injection needle.

The route of beta-8 integrin subunit or beta-8 integrin subunit antibody administration is in accord with known methods, e.g. injection or infusion by intravenous, intraperitoneal, intracerebral, intramuscular, intraocular, intraarterial, or intralesional routes, or by sustained release systems as noted below. The beta-8 integrin subunit is administered continuously by infusion or by bolus injection Beta-8 integrin subunit antibody is administered in the same fashion, or by administration into the blood stream or lymph.

Suitable examples of sustained-release preparations include semipermeable polymer matrices in the form of shaped articles, e.g. films, or microcapsules Sustained release matrices include polyesters, hydrogels, polylactides (U.S. Pat. No. 3,773,919, EP 48,481), copolymers of L-glutamic acid and gamma ethyl-L-glutamate (Sidman et al., *Bipolymers,* 22:547–556 [1983], poly (2-hydroxyethyl-methacrylate) (Langer et al., *J. Biomed. Mater. Res.,* 15:167–277 [1981] and Langer, *Chem. Tech.,* 12:98–105 [1982]), ethylene vinyl acetate (langer et al., supra) or poly-D-(−)-3-hydroxybutyric acid (EP 133,988) Sustained-release beta-8 integrin compositions also include liposomally entrapped beta-8 integrin subunit Liposomes containing beta-8 integrin subunit are prepared by methods known per se: DE 3,218,121; Epstein et al., Proc. Natl. Acad. Sci. USA, 82:3688–3692 (1985); Hwang et al., *Proc. Natl. Acad. Sci. USA,* 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324 Ordinarily the liposomes are of the small (about 200–800 Angstroms) unilamelar type in which the lipid content is greater than about 30 mol % cholesterol, the selected proportion being adjusted for the optimal beta-8 integrin subunit therapy.

Another use of the present invention comprises incorporating beta-8 integrin subunit polypeptide into formed articles. Such articles can be used in modulating cellular migration, such as the migration of granule cells into the molecular layer of the cerebellum during differentiation of brain cells. In addition, cell migration during wound healing or tumor invasion may be modulated with these articles.

An effective amount of beta-8 integrin subunit to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer the beta-8 integrin subunit until a dosage is reached that achieves the desired effect. The progress of this therapy is easily monitored by conventional assays.

4. Beta-8 Integrin Subunit Antibody Preparation

Polyclonal antibodies to the beta-8 integrin subunit generally are raised in animals by multiple subcutaneous (sc) or intraperitoneal (ip) injections of the beta-8 integrin subunit and an adjuvant. It may be useful to conjugate the beta-8 integrin subunit or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic arthydride, $SOCl_2$, or $R^1N{=}C{=}NR$, where R and $R^1$ are different alkyl groups.

Animals are immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to 1/10 the original amount of conjugate in Freund's complete adjuvant by subcutaneous injection at multiple sites 7 to 14 days later animals are bled and the serum is assayed for anti-beta-8 integrin titer. Animals are boosted until the titer plateaus Preferably, the animal is boosted with the conjugate of the same betaintegrin subunit, but conjugated to a different protein and/or through a different cross-linking agent Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The monoclonal antibody preferably does not cross-react with other known beta integrin subunit polypeptides 5. Uses of Beta-8 Integrin and its Antibodies The nucleic acid encoding the beta-8 integrin subunit may be used as a diagnostic for tissue specific typing. For example, such procedures as in situ hybridization, and northern and Southern blotting, and PCR analysis may be used to determine whether DNA and/or RNA encoding the beta-8 integrin subunit are present in the cell type(s) being evaluated. In particular, the nucleic acid may be useful as a specific probe for certain types of tumor cells such as, for example, brain tumor, gliomal, other tumor cells that are neuronal in origin, and certain other non-neuronal carcinomas such as adenocarcinoma, osteocarcinoma, and lung carcinoma Probes based on the nucleic acid or polypeptide sequences of the beta-8 integrin subunit may also be used to locate additional, novel, beta integrin subunits.

Isolated beta-8 integrin subunit polypeptide may be used in quantitative diagnostic assays as a standard or control against which samples containing unknown quantities of beta-8 integrin subunit may be compared.

Beta-8 integrin subunit antibodies are useful in diagnostic assays for beta-8 integrin expression in specific cells or tissues. The antibodies are labeled in the same fashion as the beta-8 integrin subunit described above and/or are immobilized on an insoluble matrix.

Beta-8 integrin subunit antibodies also are useful for the affinity purification of the beta-8 integrin subunit from recombinant cell culture or natural sources. The beta-8 integrin subunit antibodies that do not detectably cross-react with other beta integrin subunits can be used to purify beta-8 integrin subunit free from other known beta integrins.

Suitable diagnostic assays for the beta-8 integrin subunit and its antibodies are well known per se. Such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the beta-8 integrin subunit and for substances that bind the beta-8 integrin subunit, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the beta-8 integrin subunit or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label beta-8 integrin subunit nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels See, for example, U.S. Pat. Nos. 3,940,475 (fluorimetry) and 3,645,090 (enzymes); Hunter et al., *Nature,* 144:945 (1962); David et al., *Biochemistry,* 13:1014–1021 (1974); Pain et al., *J. Immunol. Methods,* 40:219–230 (1981); and Nygren, *J. Histochem. and Cytochem.,* 30:407–412 (1982) Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, New York, 1981), pp. 147–166. Such bonding methods are suitable for use with beta-8 integrin or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde crosslinking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the beta-8 integrin subunit or its immunologically active fragments are conjugated with a bifunctional organic bridge to an enzyme such as peroxidase. Conjugates are selected for use with anti-beta-8 integrin subunit so that binding of the antibeta-8 integrin inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of beta-8 integrin subunit or beta-8 integrin subunit antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-beta-8 integrin subunit monoclonal antibody as one antibody and a polyclonal anti-beta-8 integrin subunit antibody as the other is useful in testing samples for beta-8 integrin activity.

The foregoing are merely exemplary diagnostic assays for beta-8 integrin and antibodies. Other methods now or hereafter developed for the determination of these analytes are included within the scope hereof, including the bioassays described above.

All references cited in this specification are expressly incorporated by reference The following examples are offered by way of illustration and not by way of limitation

EXAMPLES

Example 1: Cloning and Sequencing of Rabbit and Human Beta-8 Integrin

Beta-8 integrin was initially cloned from a rabbit placental cDNA library, constructed as follows: Total RNA was isolated from rabbit placental tissue by guanidium thiocyanate extraction (McDonald et al., *Meth. Enzymol,* 152:219 [1987]). Poly(A)$^+$ RNA was purified from 2 mg of total placental RNA using MAP paper (Amersham Corp) Double-stranded cDNA was synthesized from poly(A)$^+$RNA using oligo(dT) primer. cDNA fragments larger than 2–3 kilobase pairs were purified on a 5% polyacrylamide gel and ligated to EcoRI linkers using standard procedures, Linkered cDNA was ligated into lambda gt10 (Stratagene) and packaged using Gigapack Gold II (Stratagene).

Approximately $16\times10^6$ recombinant phage of the oligo (dT) primed rabbit placental library (unamplified) were initially screened with three $^{32}$P-labelled probes. The first probe was oligonucleotide 1, a published probe which has 54 of 97 nucleotides conserved between the beta-1, beta-2 and beta-3 integrins and is known to hybridize to both rabbit and human beta-1, beta-3, and beta-5 integrin subunits. This probe has the sequence AAGCAGAGTG TGTCACGGAA CCGAGATGCC CCAGAGGGTG GCTTTGATGC CATCATGCAG GCTACAGTCT GTGATGAAAA GATTGGCTGG AGGAATG (SEQ. ID. NO. 1 ) (see the probe identified as intb5 in McLean et al., *J. Biol. Chem.* 265:17126 [1990]). This first oligonucleotide probe is composed of the human beta-3 integrin subunit sequence that is conserved at the DNA level in all known beta integrins.

In addition, probes that encode the rabbit beta-1 integrin subunit and the rabbit beta-5 integrin were used to screen out positives that code for these more abundant beta integrins The second probe was oligonucleotide 2, a beta-5 integrin subunit oligonucleotide (5'-ACGTGCGAGAAGTGCCCCACCTGCCCGGATGCTTG CAGCACCAAG-3'[SEQ. ID. NO. 2])that hybridizes only to rabbit beta-5 subunit sequences. A third probe was a partial rabbit beta-1 integrin subunit cDNA.

Prehybridization and hybridization conditions were 5X SSC (SSC: 150 mM NaCl, 15 mM trisodium citrate), 005M sodium phosphate, pH 6.8, 5X Denhardt's solution, 10% dextran sulfate, and 20μg/ml boiled, sheared salmon sperm DNA Formamide was added to a final concentration of either 20% (for oligonucleotide probes) or 50% (for cDNA probes). Prehybridization and hybridization were at 42° C., and the filters were washed for 30 minutes with either 2X SSC at 45° C. (oligonucleotide probes) or with 01X SSC at 65° C. (cDNA probes). The filters were exposed overnight to x-ray film with two intensifying screens at −70° C. The cDNA inserts from six phage isolates that hybridized to oligonucleotide 1, but not to rabbit beta-1 integrin subunit cDNA or to oligonucleotide 2 were excised from the lambda gt10 vector and were subcloned into the bacteriophage M13 and the DNA was partially sequenced. Two of these clones contained sequences that overlapped. This overlapping sequence was designated Ra-1, and it was found to be similar to, but distinct from, beta integrin subunits 1–7. This Ra-1 clone was thus identified as a novel beta integrin subunit, named the beta-8 integrin subunit. The Ra-1 (beta-8 integrin subunit) clone was used to screen filters from a second, randomly primed rabbit placental cDNA library (constructed as described for the oligo (dT) library, except cDNA was primed using random hexamers (Amersham Corp). Three additional beta-8 integrin subunit isolates were obtained from this rabbit placental library.

The full-length beta-8 integrin subunit sequence from the rabbit was inferred from two overlapping clones to be 2972 nucleotides (as shown in FIG. 1 ). This comprises an open reading frame of 2304 nucleotides (nt), a 5' untranslated region (UTR) of 651 nt, and a 3' UTR of 17 nt.

The rabbit beta-8 integrin subunit cDNA was subsequently used to screen human cDNA libraries to isolate the human homolog of the beta-8 integrin subunit. Initially, an amplified human placental cDNA library was screened as follows: Approximately $1.1\times10^5$ recombinant phage of a randomly primed human placental library were screened with the rabbit beta-8 integrin subunit cDNA probe at medium stringency (the same hybridization solution as described above, but containing 30% formamide) and these filters were washed with 1X SSC at 55° C. This library yielded a single clone of approximately 900 base pairs (bp) that comprised about 40% of the coding sequence of the human beta-8 integrin subunit plus a small amount of 3' UTR.

Using PCR analysis, it was determined that beta-8 integrin subunit mRNA was present in MG-63 human osteosarcoma cells. Therefore, a MG-63 cDNA library was screened with the human beta-8 integrin subunit partial cDNA (obtained from the human placental library) as a probe. The randomly primed MG-63 library was constructed using a method similar to that described above for the rabbit placental libraries, except the starting material was $5\times10^9$ MG-63 cells, poly(A+) was prepared using poly(U) Sepharose affinity chromatography and cDNA fragments greater than 3 kb were ligated into lambda gt10. Packaging was done using Gigapack Gold IIXL (Stratagene). This library yielded three overlapping clones, the longest of which, clone Hu-2, is 3789 bp (FIG. 2) and contains an open reading frame of 2307 nucleotides, a 5' UTR of 680 nucleotides and a 3' UTR of 802 nucleotides.

Both strands of the rabbit and human beta-8 integrin subunit clones were sequenced. The beta-8 integrin subunit isolates were subcloned into the BLUESCRIPT II vector (Stratagene) and double stranded DNA was sequenced using the Sequenase version 20 kit (U.S. Biochemical) and synthetic oligonucleotide primers. To facilitate sequence determination of long stretches of DNA, nested deletions were created by exonuclease III and mung bean nuclease (using a kit obtained from Stratagene). The rabbit and human beta-8 integrin subunit polypeptides encoded by the cDNAs obtained are 768 (calculated molecular weight of 84,406) and 769 (calculated molecular weight of 85,631) amino acid residues, respectively as determined from translation of the cDNA sequences. These beta-8 integrin subunit amino acid sequences are very similar (89% at the amino acid level). The beta-8 integrin subunit contains 54 cysteine residues of which all but one are conserved colinearly between rabbit and human. The human beta-8 integrin subunit amino acid sequence was found to be very distinct from known beta integrins; the beta-8 integrin subunit amino acid sequence shares approximately 35%, 32%, 34%, 31%, 34%, 37%, and 31% identity with human beta integrin subunits 1 through 7, respectively.

Example 2: Detection of The Beta-8 Integrin Subunit mRNA Expression by PCR

The method of PCR analysis was used to detect expression of the beta-8 integrin subunit mRNA in several human cell lines. The cell lines evaluated were: 293 human kidney adenocarcinoma (ATCC number CRL 1573), MG-63 human osteosarcoma (ATCC number CRL 1427), UCLA-P3 human lung carcinoma (obtained from Dr. Donald Morton, University of California at Los Angeles) and HEL human erythroleukemia (obtained from the University of California at San Francisco Cell Culture Facility). PCR primers were derived from the human beta-8 integrin subunit nucleotide sequence. Single stranded cDNA was synthesized by priming 1 μg of poly(A)$^+$ RNA from several cell lines (prepared as described by Bodary et al., *J. Biol. Chem.*, 265:5938 [1990]) with random hexanucleotides and extending with avian myoblastosis virus reverse transcriptase (cDNA synthesis kit, Amersham Corp.). One twentieth of the reaction product was amplified using the PCR GeneAmp kit, (Perkin-Elmer-Cetus), with 50 pmol of oligonucleotide primers (24 mers) in a 100 μl reaction volume, on a Perkin-Elmer-Cetus DNA thermal cycler. PCR conditions were: cycle 1, denaturation at 98° C. for 2 min., annealing at 45° C. for 30 sec., extension at 72° C. for 30 sec.; cycles 2–5, denaturation at 98° C. for 15 sec., annealing and extensions as for cycle 1, cycles 6–35, denaturation at 96° C. for 30 sec., annealing and extension as for cycle 1 except that extension times were incremented by 1 sec./cycle. One-tenth of the reaction product was analyzed on a 6.4% acrylamide gel. Primers (5'-TTCATCATTTTTCATAGTTACATTC-3' and 5'CATTAAGTGTTTAAAAATCTTTTT-3'[SEQ. ID. NO. 9]) were chosen that gave a predicted amplified DNA product of 276 bases.

The results indicated that 293, MG-63, and UCLA P-3 cells expressed beta-8 integrin subunit message, while HEL cells did not.

Example 3: Detection of Beta-8 Integrin mRNA Expression by Northern Analyses

The rabbit beta-8 integrin subunit cDNA was used as a probe in northern analyses to investigate expression of beta-6 integrin subunit mRNA in various rabbit tissues. A pregnant rabbit was sacrificed and its tissues (whole fetus, heart, lung, pancreas, spleen, brain, ovary, bone marrow, whole blood, uterus, skeletal muscle, kidney, liver and placenta) were dissected. Total mRNA was prepared from these tissues as follows: Total RNA was obtained from one gram of each tissue by guanidium thiocyanate extraction. Poly(A)$^+$ RNA was purified from 500 μg of total RNA using oligo(dT) cellulose columns (Stratagene). One half of this poly(A)$^+$ RNA was then fractionated on a denaturing 1.2% agarose gel containing 2% formaldehyde and blotted to Blotrace membrane (Gelman Sciences) overnight. The membrane was prehybridized and hybridized as for the cDNA library screening except that the formamide concentration was increased to 50% and all solutions (including wash solutions) contained 0.2% SDS. The membrane was probed with randomly primed $^{32}$P-labelled, partial rabbit beta-8 integrin subunit, beta-1 integrin subunit, and beta-3 integrin subunit cDNAs and washed with 0.1X SSC at 60° C. The membrane was stripped before addition of new probe by washing in 0.2% SDS at 800 with gentle agitation, for 5 minutes.

Tissues that were positive for an approximately 8 kilobase (kb) beta-8 integrin subunit message included kidney, brain, placenta, ovary and uterus. To demonstrate that this pattern of expression was specific for the beta-8 integrin subunit, the blot with the cDNA probes that encoded rabbit beta-1 integrin subunit and beta-3 integrin subunit was reprobed. In these experiments, an approximately 3.5 kb beta-1 integrin subunit message was detected in all tissues. In addition, two beta-3 integrin subunit messages of about 3.5 and 5.5 kb were detected in only uterus and bone marrow. From these and the sequencing results, the beta-8 integrin subunit appears to be a distinct and separate beta integrin subunit.

Example 4: Expression and Detection of the Human Beta-8 Intefirin Subunit

The 3789 bp human beta-8 integrin subunit cDNA was subcloned into the pRK5 expression vector described in EP 07/560,482 and human embryonic kidney 293 cells were transfected with this construct using the standard calcium phosphate precipitate method (Sambrook et al., supra). Cells were plated on day I at a concentration of $2\times10^6$, exposed to a calcium phosphate precipitate containing 10 μg of expression plasmid or no DNA (control cells) on day 2 and harvested on day 4 with 5 mM EDTA in Ca2 +/Mg2 +-free PBS (phosphate buffered saline, see section B.12 of Sambrook et al., supra).

Cells ($1–2\times10^{-7}$) were surface labelled with 1 mCi $Na^{125}$ (Amersham Corp.) and 100 μg lactoperoxidase (Sigma) in the presence of 0.0015% $H_2O_2$. After labelling for 10 min. at room temperature, cells were washed once with 5 mM Kl in PBS and then twice with PBS. Labelled cells were solubilized for 30 min. at 4° C. in 0.5 ml of Extraction Buffer (1% Triton X-100, 20 mM Tris pH 7.5, 150 mM NaCl and 1 mM $CaCl_2$) with occasional vortexing. Cellular debris was then pelleted by centrifugation at 5000×g for 5 min., end the cell extract supernatant diluted to 0.5% Triton X-100 by the addition of 0.5 ml Extraction Buffer without Triton X-100.

The beta-8 integrin subunit polypeptide was detected by immunoprecipitation using anti-peptide polyclonal antibodies specific for the beta-8 integrin subunit. The synthetic peptide $H_2$N-EEIKMDISKLNAHETFRCNF-COOH (SEQ. ID. NO. 7), comprising C-terminal human beta-8 integrin residues predicted by the cDNA sequence was used as an immunogen. The peptide was synthesized by F-moc chemistry using a Milligen 9050 peptide synthesizer from Biosearch. For immunization, ten mg of this peptide was coupled to 20 mg of soybean trypsin inhibitor using sulfo-MBS (Pierce) as per manufacturer's specifications. Rabbits were immunized, by subcutaneous injection, with the equivalent of 200 μg of peptide at three week intervals. High titer bleeds were obtained at about two to three months after the initial immunization.

For the immunoprecipitation, four hundred microliters of the labelled cell extract was incubated with 1/100 volume of antibody (ascites, culture supernatant or antiserum) at 4° C. overnight, and immunoprecipitations were carried out using Protein G Sepharose™ 4FF (Pharmacia) after first preclearing with SEPHAROSE™ CL-4B (Pharmacia). Protein G SEPHAROSE™ beads were washed three times with 0.05% Tween 20, 20mM Tris pH 8, 120 mM NaCl, 2 mM $CaCl_2$. Proteins precipitated from the labelled cell extracts were solubilized by heating in sample buffer and analyzed by separation on a 7.5% SDS-polyacrylamide gel followed by autoradiography.

The results indicated that the beta-8 integrin subunit polypeptide is expressed on the surface of transformed 293 cells but not on the surface of control 293 cells.

Example 5: Detection of the beta-8/alpha-v Complex

Human embryonic kidney 293 cells, transfected as described in the previous example, were used to demonstrate the presence of a novel beta-8/alpha-v integrin complex. These cells endogenously express various alpha integrin subunits, including alpha-v. The beta-8 integrin transfected cell proteins were prepared for immunoprecipitation as described in Example 4.

Monoclonal antibodies against several different alpha integrin subunits were used in the immunoprecipitations in order to identify with which alpha subunit the beta-8 integrin formed a complex. Mouse monoclonal antibodies against alpha-1 (antibody TS2/7, Hemler et al., *J. Immunol.*, 132:3011 [1984]), alpha-2 (antibody P1H5, Wayner et al., supra), alpha-3 (antibody P1B5, Wayner et al., supra), alpha-5 (antibody P1D6, Wayner et al., supra), alpha-v (antibody 13C2, obtained from M. Horton, Dept. of Haematology, St. Bartholomew's Hospital, London, England) and rat monoclonal antibody against alpha-6 (antibody GoH3), Sonnenberg et al., *J. Biol. Chem.*, 262:10376 [1987]) were tested. The immunoprecipitations were conducted as described in Example 4.

The results of these immunoprecipitations indicated that the alpha-v subunit readily associates with and forms a complex with the beta-8 integrin subunit in transfected human embryonic kidney 293 cells, while in 293 cells, associations were not made with alpha integrin subunits 1,2,3,5, and 6.

We claim:

1. An isolated antibody that specifically binds to beta-8 integrin subunit polypeptide wherein said antibody does not specifically bind to beta integrin subunit polypeptides selected from the group consisting of 1, 2, 3, 4, 5, 6 and 7.

2. An isolated antibody that specifically binds to a complex comprising a beta-8 integrin subunit polypeptide, which peptide is associated with an alpha v integrin subunit polypeptide wherein said antibody does not specifically bind to a complex comprising an alpha v integrin subunit polypeptide associated with a beta integrin subunit polypeptide selected from the group of beta integrin subunit polypeptides consisting of 1, 2, 3, 4, 5, 6 and 7.

3. The antibody of claim 1 which is a monoclonal antibody.

4. The antibody of claim 2 which is a monoclonal antibody.

5. The antibody of claim 1 wherein said beta-8 integrin subunit polypeptide is human.

6. The antibody of claim 2 wherein said beta-8 integrin subunit polypeptide and said alpha integrin subunit polypeptide are human.

* * * * *